United States Patent
Zhou

(10) Patent No.: US 9,833,140 B2
(45) Date of Patent: Dec. 5, 2017

(54) PORTABLE CORNEAL TOPOGRAPHER

(71) Applicant: Smart Vision Labs, Inc., New York, NY (US)

(72) Inventor: Yaopeng Zhou, New York, NY (US)

(73) Assignee: SMART VISION LABS, INC., New York, NY (US)

(*) Notice: Subject to any disclaimer, the term of this patent is extended or adjusted under 35 U.S.C. 154(b) by 27 days.

(21) Appl. No.: 14/991,278

(22) Filed: Jan. 8, 2016

(65) Prior Publication Data

US 2016/0198946 A1    Jul. 14, 2016

Related U.S. Application Data

(60) Provisional application No. 62/247,399, filed on Oct. 28, 2015, provisional application No. 62/128,562, (Continued)

(51) Int. Cl.
*A61B 3/14* (2006.01)
*A61B 3/107* (2006.01)
(Continued)

(52) U.S. Cl.
CPC ............ *A61B 3/107* (2013.01); *A61B 3/0025* (2013.01); *A61B 3/0091* (2013.01);
(Continued)

(58) Field of Classification Search
CPC ....... A61B 3/0025; A61B 3/102; A61B 3/107; A61B 3/14
(Continued)

(56) References Cited

U.S. PATENT DOCUMENTS

| 5,011,276 A | 4/1991 | Iwamoto |
| 5,617,157 A | 4/1997 | Shalon et al. |

(Continued)

FOREIGN PATENT DOCUMENTS

| EP | 1882444 | 1/2008 |
| WO | 2004017825 A1 | 3/2004 |

(Continued)

OTHER PUBLICATIONS

International Search Report and Written Opinion dated Jan. 30, 2015 for PCT/US2014/059363.

(Continued)

*Primary Examiner* — Hung Dang
(74) *Attorney, Agent, or Firm* — Lowenstein Sandler LLP

(57) ABSTRACT

Portable corneal topographers and portable corneal topographer modules are disclosed. In one embodiment, a corneal topographer module comprises a housing having a first aperture and a second aperture formed therethrough; and a plurality of optical components disposed within the housing. The plurality of optical components are arranged to direct light generated by a light source through the first aperture to the cornea via a first optical channel when a cornea of a patient's eye is located adjacent to the first aperture; and direct reflected light from the cornea into the housing through the first aperture and to a light detector of a mobile device via a second optical channel when the corneal topographer module is mechanically coupled to the mobile device.

19 Claims, 29 Drawing Sheets

Related U.S. Application Data filed on Mar. 5, 2015, provisional application No. 62/110,663, filed on Feb. 2, 2015, provisional application No. 62/101,478, filed on Jan. 9, 2015.

(51) Int. Cl.

| | | |
|---|---|---|
| *G01M 11/02* | (2006.01) | |
| *A61B 3/10* | (2006.01) | |
| *A61B 3/00* | (2006.01) | |
| *G02B 3/00* | (2006.01) | |
| *A61B 3/15* | (2006.01) | |
| *A61B 5/00* | (2006.01) | |
| *G06T 7/00* | (2017.01) | |
| *H04N 5/225* | (2006.01) | |
| *A61B 3/12* | (2006.01) | |

(52) U.S. Cl.
CPC .............. *A61B 3/1015* (2013.01); *A61B 3/12* (2013.01); *A61B 3/14* (2013.01); *A61B 3/152* (2013.01); *A61B 5/6898* (2013.01); *G01M 11/0207* (2013.01); *G01M 11/0228* (2013.01); *G02B 3/0075* (2013.01); *G06T 7/0014* (2013.01); *H04N 5/2252* (2013.01); *H04N 5/2254* (2013.01); *G02B 3/0006* (2013.01); *G06T 2207/30041* (2013.01)

(58) Field of Classification Search
USPC ....... 351/206, 246, 205, 221, 208, 109, 210, 351/211, 212
See application file for complete search history.

(56) References Cited

U.S. PATENT DOCUMENTS

| | | | |
|---|---|---|---|
| 6,264,328 | B1 | 7/2001 | Williams et al. |
| 9,066,683 | B2 | 6/2015 | Zhou |
| 2003/0142271 | A1 | 7/2003 | Ross et al. |
| 2011/0299036 | A1 | 12/2011 | Goldenholz |
| 2012/0320340 | A1 | 12/2012 | Coleman, III |
| 2013/0027668 | A1 | 1/2013 | Pamplona et al. |
| 2013/0135584 | A1 | 5/2013 | Alasaarela et al. |
| 2015/0098060 | A1 | 4/2015 | Zhou |
| 2015/0103317 | A1 | 4/2015 | Goldfain et al. |
| 2015/0126810 | A1 | 5/2015 | Wood et al. |
| 2015/0164318 | A1 | 6/2015 | Zhou |
| 2015/0313467 | A1 | 11/2015 | Sakai et al. |
| 2016/0128562 | A1 | 5/2016 | Durr et al. |
| 2016/0128566 | A1* | 5/2016 | Durr ............. A61B 3/1015 351/206 |
| 2016/0198946 | A1 | 7/2016 | Zhou |
| 2016/0202141 | A1 | 7/2016 | Zhou |
| 2016/0205298 | A1 | 7/2016 | Zhou |

FOREIGN PATENT DOCUMENTS

| | | |
|---|---|---|
| WO | 2012177544 | 12/2012 |
| WO | 2015003062 | 1/2015 |

OTHER PUBLICATIONS

International Search Report and Written Opinion dated Jun. 27, 2015 for PCT/US2016/012678.

Vitor F. Pamplona et al., "NETRA: Interactive Display for Estimating Refractive Errors and Focal Range", in ACM SIGGRAPH 2010 papers, Hughes Hoppe (Ed), ACM, New York, NY, USA, Article 77, 8 pages.

\* cited by examiner

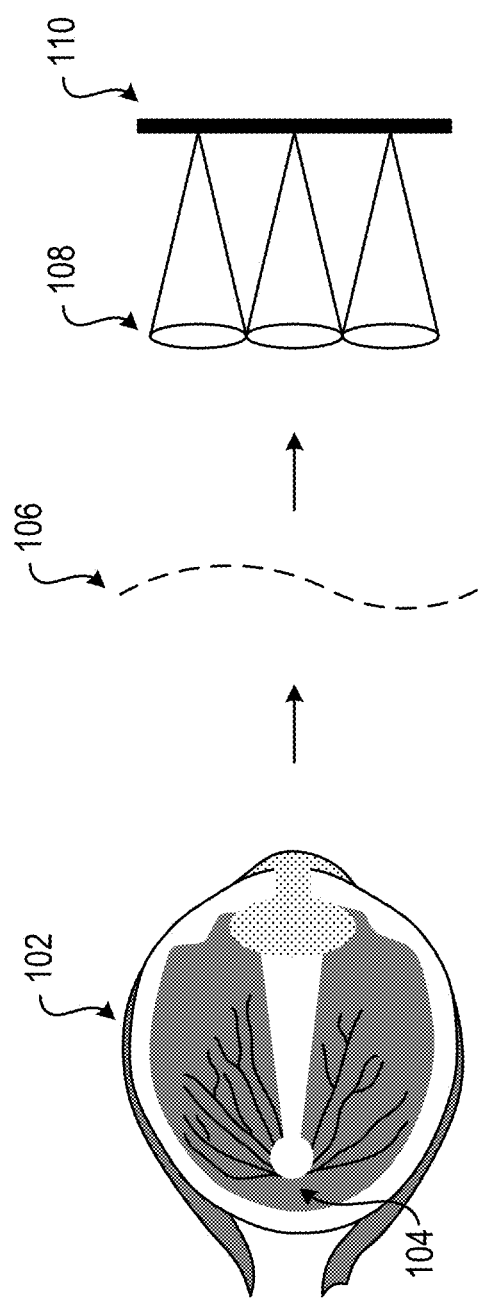

PORTABLE CORNEAL TOPOGRAPHER

CROSS-REFERENCE TO RELATED APPLICATIONS

This application claims the benefit of priority of each of U.S. Provisional Patent Application Ser. No. 62/247,399, filed on Oct. 28, 2015, U.S. Provisional Patent Application Ser. No. 62/128,562, filed on Mar. 5, 2015, U.S. Provisional Patent Application Ser. No. 62/110,663, filed on Feb. 2, 2015, and U.S. Provisional Patent Application Ser. No. 62/101,478, filed on Jan. 9, 2015, the disclosures of which are hereby incorporated by reference herein in their entireties.

TECHNICAL FIELD

Embodiments of the present disclosure relate to optical devices for detecting and measuring refractive errors of a patient's eye, retinal and corneal imaging, and prescription lens analysis.

BACKGROUND

In the United States, vision tests are not routinely provided to children under the age of 6, with only 14% of children under the age of 6 having had a vision exam. In addition, over 500 million people worldwide suffer from refractive error-related illness, with more than 90% of these people being in developing countries. Such conditions are likely to worsen over time if not identified and corrected early.

Several factors may prohibit both early detection and detection in general. One is communication, as may be the case with a small child who cannot clearly indicate that he/she is experiencing an ailment or in a developing country in which a patient may not be able to communicate effectively with a care provider. Another factor is cost, which may be particularly limiting in developing countries as equipment for detecting refractive errors can be expensive. Moreover, well-trained personnel for operating the equipment and analyzing the results may be inaccessible or have limited availability.

BRIEF DESCRIPTION OF THE DRAWINGS

The embodiments of the present disclosure are illustrated by way of example and not by way of limitation, and will become apparent upon consideration of the following description, taken in conjunction with the accompanying drawings, in which:

FIG. 1A depicts an eye, a wavefront generated by reflected light from the eye's retina, and an array of lenses that focus the reflected light onto a light detector;

DETAILED DESCRIPTION

Figure 1B:
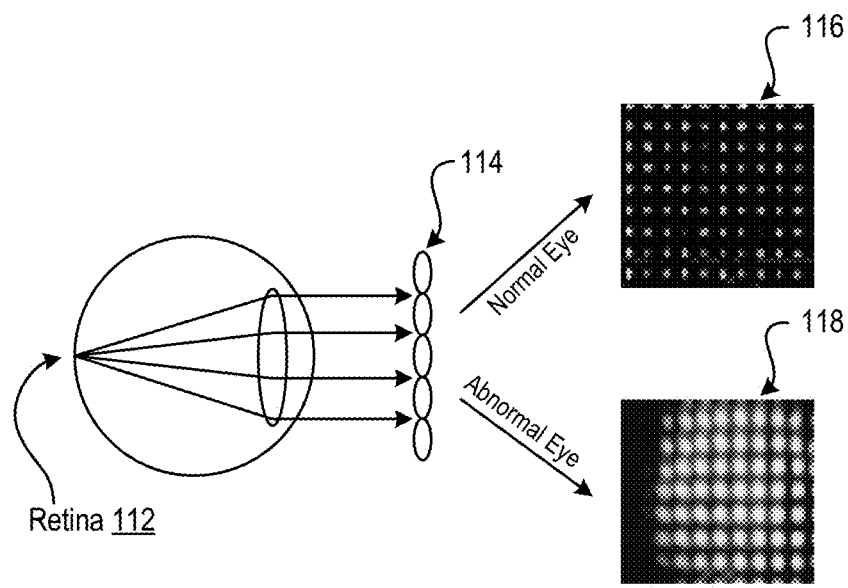
FIG. 1B depicts differences in Shack-Hartmann spots measured for a normal eye and an eye with refractive errors.

The embodiments described herein relate to optical devices for use by ophthalmologists, optometrists, and other medical practitioners to perform various medical evaluations, including detecting and measuring refractive errors of a patient's eye, obtaining images of the patient's retina (fundus photography), and mapping the surface curvature of the cornea (corneal topography). Other embodiments relate to a lensmeter for determining a prescription of a lens of a pair of glasses. An optical device as disclosed herein may be implemented as a self-contained optical device that include optical components, one or more light sources, and one or more light detectors, or may be implemented as an optical device module that can be coupled to one or more additional devices such that the combination forms a fully-functional optical device.

In certain embodiments, light generated by a light source, such as a laser, is directed to a patient's eye. The light source may be an on-board light source of the optical device, or may be provided by an external device (e.g., a mobile device such as a smartphone) coupled to the optical device. Reflected light from the eye is captured by an on-board or external light detector (e.g., a camera), and may be subsequently processed by software of a processing device of the optical device, a mobile device, or a separate remote device (e.g., a computer or server of a medical practitioner).

One advantage of the present embodiments is that of providing a self-contained portable wavefront aberrometer capable of measuring aberrations of the eye and processing captured image data or transmitting the data to another device for processing. Another advantage of the present embodiments is to provide a modular optical device that can be reversibly coupled to a portable computing device, such as a smartphone, to create a fully-functional optical device. Another advantage of the present embodiments is to provide lower-cost optical devices that leverage the imaging and/or data processing ability of a portable computing device likely to already be owned by a consumer or medical practitioner. Another advantage of the present embodiments is to provide lower-cost optical devices that could be branded by a medical practitioner and lent to a patient for use to provide the medical practitioner with multiple data sets tracking, for example, changes in refractive errors of the patient's eyes. Another advantage of the present embodiments is that a patient may obtain diagnostic measurements without a visit to the medical practitioner, and optionally, to have those measurements transmitted to the medical practitioner for diagnostic purposes or to fashion or otherwise make ready corrective lenses for purchase. The nature of the embodiments disclosed herein may reduce the costs associated with various optical devices, making such devices more feasible for home use or in areas of limited medical infrastructure, such as developing countries.

In certain embodiments, an optical device comprises a housing that encloses optical components, a light source, an image detector, and a processing device. The processing device may process captured image data completely or partially, or transmit the image data to another device for processing (e.g., via Bluetooth to a mobile computing device). As used herein, "mobile device" or "mobile computing device" may refer to a smartphone, a mobile phone, a personal digital assistant, a personal computer, a laptop, a netbook, a tablet computer, a palmtop computer, a television (e.g., a "smart TV"), or any device having a built-in camera. A mobile device may also refer to a portable camera or an optical imaging device operatively coupled to a computing device (e.g., a webcam). Smartphones are mobile phones having a computer, an illuminated screen, and a camera, among other features. Other mobile devices having a camera may be used in accordance with the subject matter of this application. For example, a mobile device that may be used in accordance with the disclosed embodiments could be a phone (or smartphone) equipped with a camera, although other devices such as tablet computers, laptop computers, certain audio or video players, and ebook readers may also be used, any of which may include a light detector (e.g., a camera) and either a processing device or a transceiver for communicating the information captured by the camera to another device with a processing device.

In certain embodiments, an optical device, such as a portable wavefront aberrometer, may comprise two separate components that are coupled together to form a single functioning unit: a module and a mobile device. The module may include a guide for positioning or attaching the module to the mobile device to provide a beam path whereby light from the light source can be directed towards the patient's eye, and provide a beam path whereby light from the light source that is reflected off the patient's eye travels through an array of microlenses (a "microlens array") and then onto the light detector of the mobile device. This separation provides the benefit of division of cost and complexity of an optical device into a module portion and a mobile device portion, with the mobile device likely being owned or available to a consumer.

Captured image data may then be processed through algorithms known in the art by an on-board processing device of the self-contained optical device, a processing device of the mobile computing device, or by a separate device to which the data is transmitted. The data may be presented to the end user in an unprocessed form, in a partially processed form, or in a post-processed format, such as an eyeglasses prescription or a Snellen fraction. Software on the mobile device may also limit the information presented to the end user and send either the unprocessed or processed data to a medical practitioner or technician for diagnostic use and/or to prepare corrective lenses.

The following description and drawings referenced herein illustrate embodiments of this application's subject matter, and are not intended to limit the scope. Those of ordinary skill in the art will recognize that other embodiments of the disclosed systems, devices, and methods are possible. All such embodiments should be considered within the scope of the claims. Reference numbers are not necessarily discussed in the order of their appearances in the drawings. Depictions of various components within the drawings, such as optical components, are illustrative and not necessarily drawn to scale.

FIG. 1A depicts an eye 102, a wavefront 106 corresponding to light reflected from the retina 104 of the eye 102, and a lens array 108 (e.g., a microlens array) that separates the reflected light and focuses it onto a light detector 110 (e.g., a two-dimensional light detector). In certain embodiments, the light detector 110 may be incorporated into a portable wavefront aberrometer module. In other embodiments, the light detector 110 may be a camera of a mobile device, such as a smartphone, and the mobile device may be mechanically coupled to a portable wavefront aberrometer module. It should be understood that the combination of the module with a smartphone in this embodiment should not limit the claims to the use of a smartphone, as any mobile device can be used with a module as disclosed herein.

FIG. 1B illustrates how reflected light from a patient's retina 112 may be captured by a light detector. The reflected light is transformed into a spot array as it passes though a microlens array 114, such as any of the microlens arrays described herein. If the eye is free of aberrations (e.g., a "normal eye"), the resulting spot array captured by the mobile device's camera may be composed of evenly distributed spots 116. If instead the eye has aberrations (e.g., an "abnormal eye"), the resulting captured spot array may have distorted spot distribution 118.

Figure 1C:
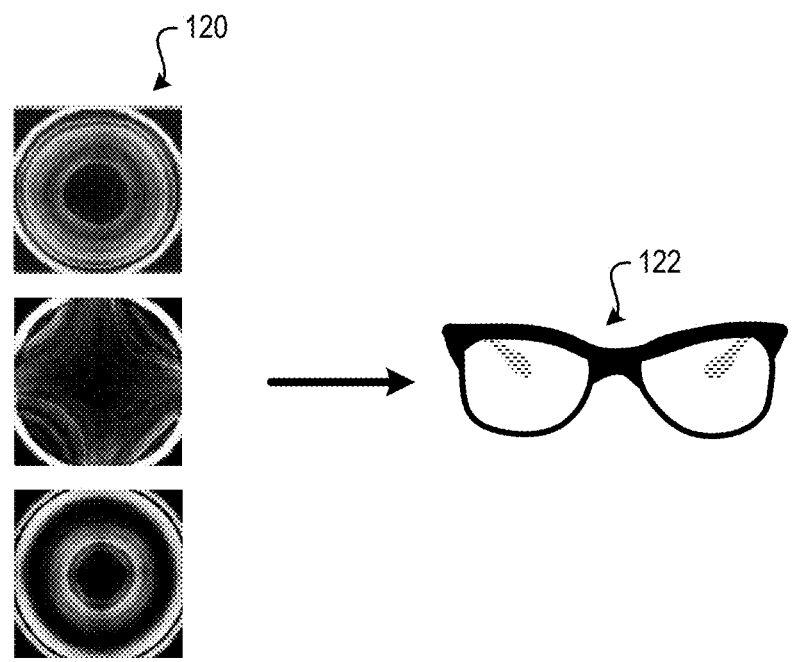
FIG. 1C depicts wavefront contour shapes representing defocus and astigmatism.

FIG. 1C depicts wavefront contour shapes representing defocus and astigmatism. The image of the spot array can be mathematically transformed though the use of algorithms known in the art by a processing device (e.g., an on-board processing device of a portable wavefront aberrometer, a processing device of a mobile device, etc.). One such transformation can be to create contour maps 120 representing the aberrations of the eye. The spot arrays may also be transformed by a processing device into an eye prescription that can be used to create corrective lenses 122 for the patient.

Although the primary source of reflected light from the patient's eye is light reflected off of the retina, a secondary source of the reflected light is that which may be reflected off the patient's cornea or crystalline lens. In certain embodiments, this corneal or lenticular reflected light may be treated as noise, and may be subtracted during processing or minimized through the use of methods and techniques known by one of ordinary skill in the art.

Figure 2A:
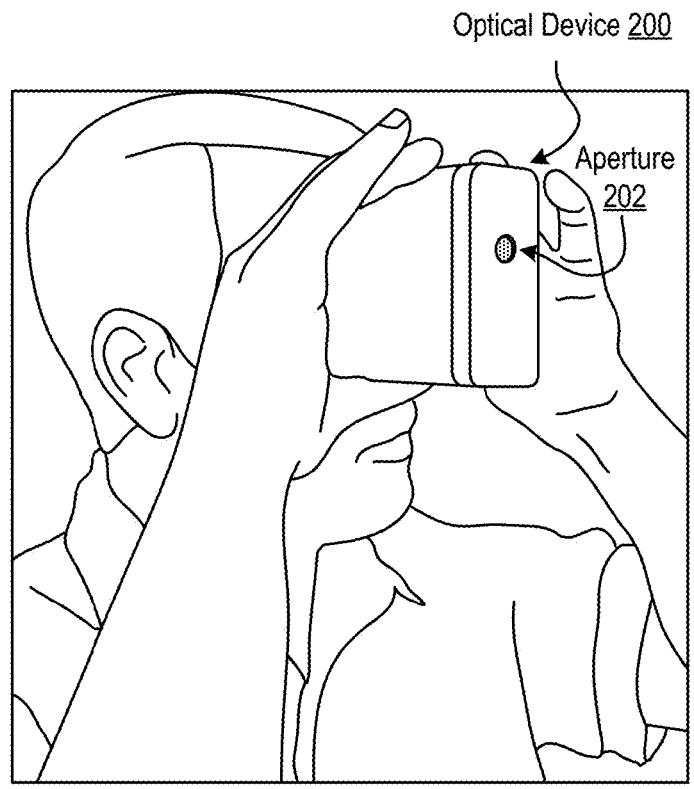
FIG. 2A is an illustration of the operation of an optical device according to an embodiment of the present disclosure.
Figure 2B:
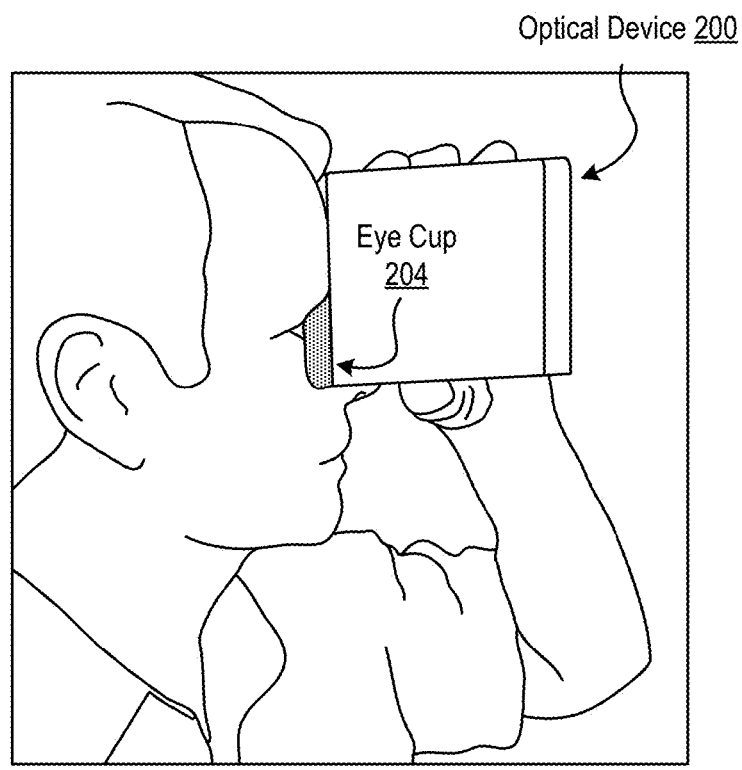
FIG. 2B is an illustration of the operation of an optical device according to an embodiment of the present disclosure.

FIGS. 2A and 2B illustrate the use of an optical device 200 according to an embodiment of the present disclosure. The optical device 200 may be a portable wavefront aberrometer, a portable fundus camera, or a portable corneal topographer, with such embodiments being described below in greater detail. In certain embodiments, the optical device 200 may utilize an open field alignment channel (or open field channel), as will be described in greater detail below. The open field alignment channel utilizes an aperture 202 that allows a patient to focus on a nearby object. Light from the object enters the aperture 202 and is directed to the patient's eye. In certain embodiments, the open field alignment channel and corresponding aperture 202 may be omitted. An eye cup 204 may improve the patient's comfort and provide stability during the measurement.

Figure 2C:
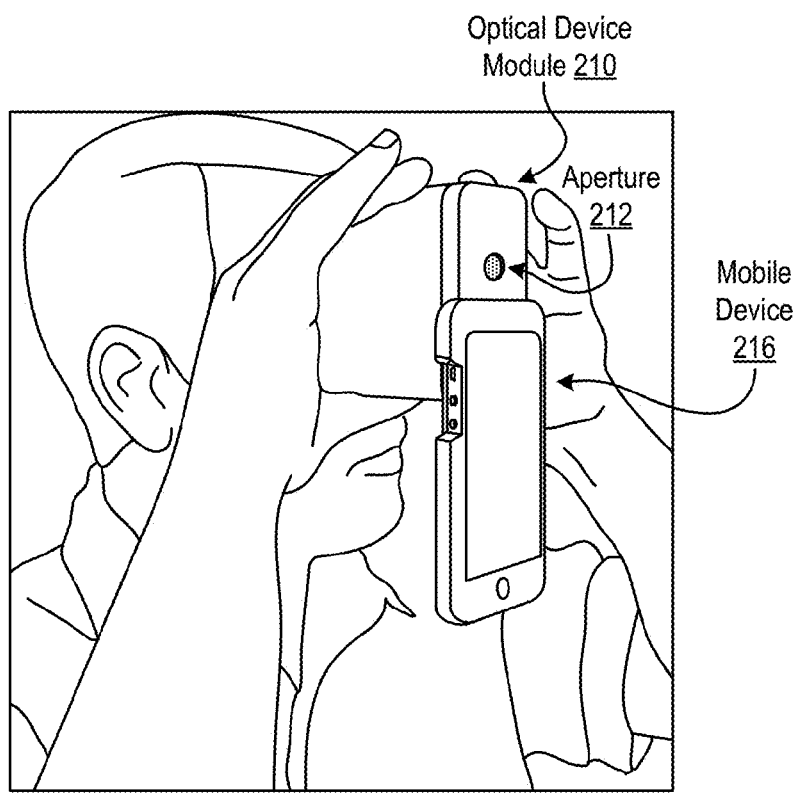
FIG. 2C is an illustration of the operation of an optical device according to an embodiment of the present disclosure.
Figure 2D:
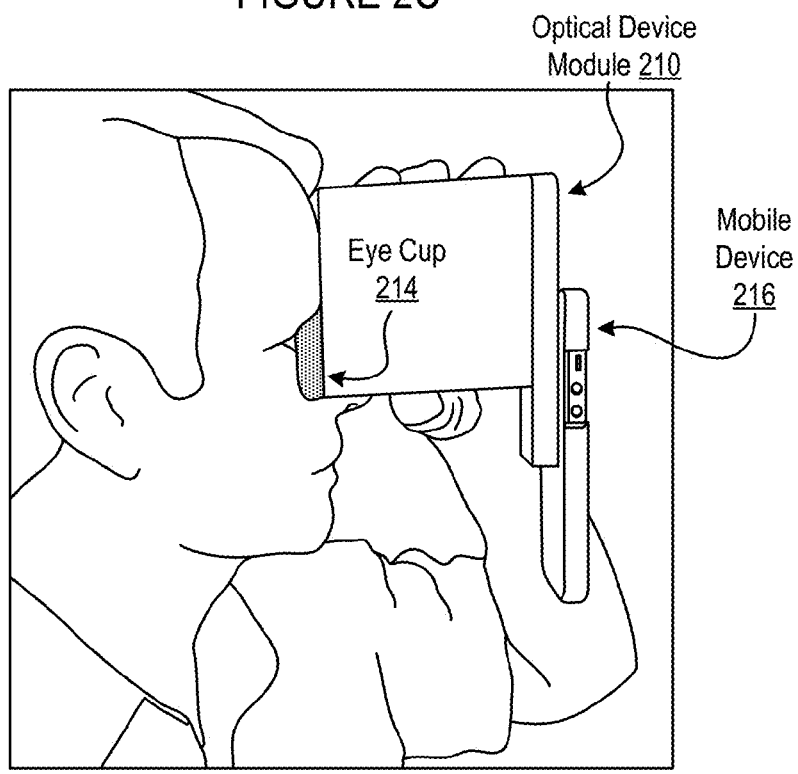
FIG. 2D is an illustration of the operation of an optical device according to an embodiment of the present disclosure.

FIGS. 2C and 2D illustrate the use of an optical device module 210 in combination with a mobile device 216. The optical device module 210 in combination with the mobile device 216 may collectively form a portable wavefront aberrometer, a portable fundus camera, or a portable corneal topographer. The mobile device 216 may be removably coupled to the optical device module 210, and may be used to capture image data and/or serve as a light source in certain embodiments. In certain embodiments, the optical device module 210 may include an open field channel and an associated aperture 212.

Figure 2E:
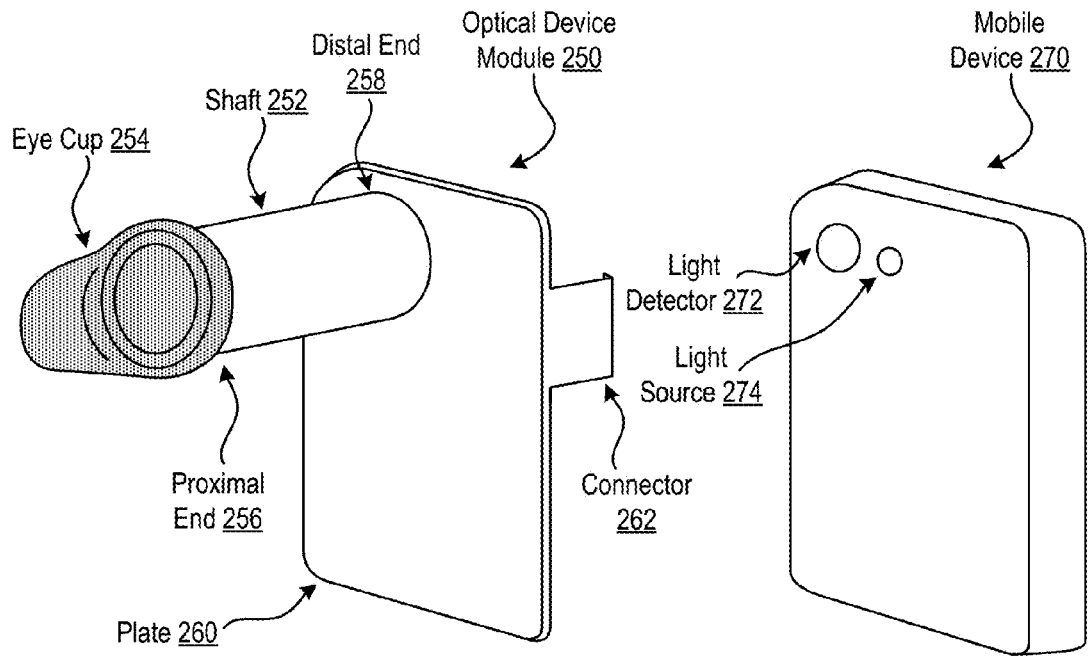
FIG. 2E is an illustration of an embodiment of an optical device module separated from a mobile device according to another embodiment of the present disclosure.
Figure 2F:
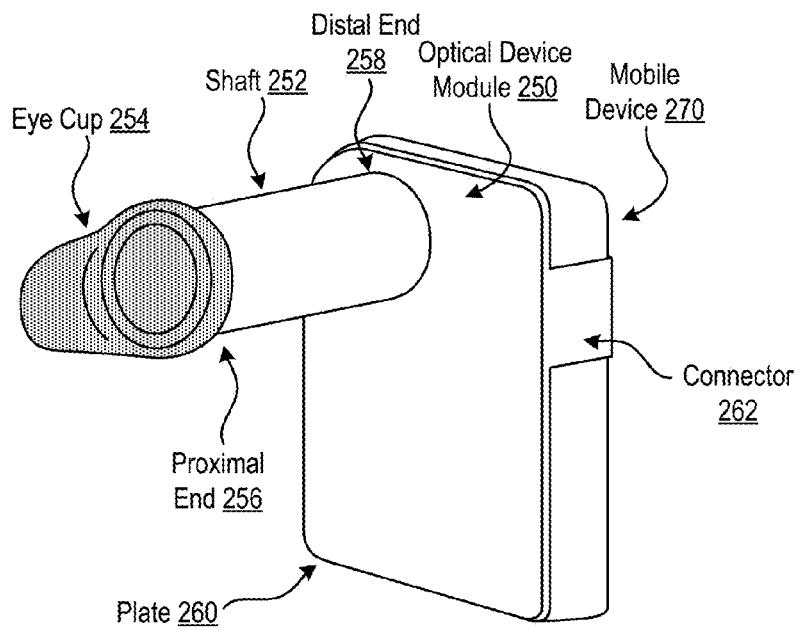
FIG. 2F is an illustration of an embodiment of an optical device coupled to a mobile device according to another embodiment of the present disclosure.
Figure 4:
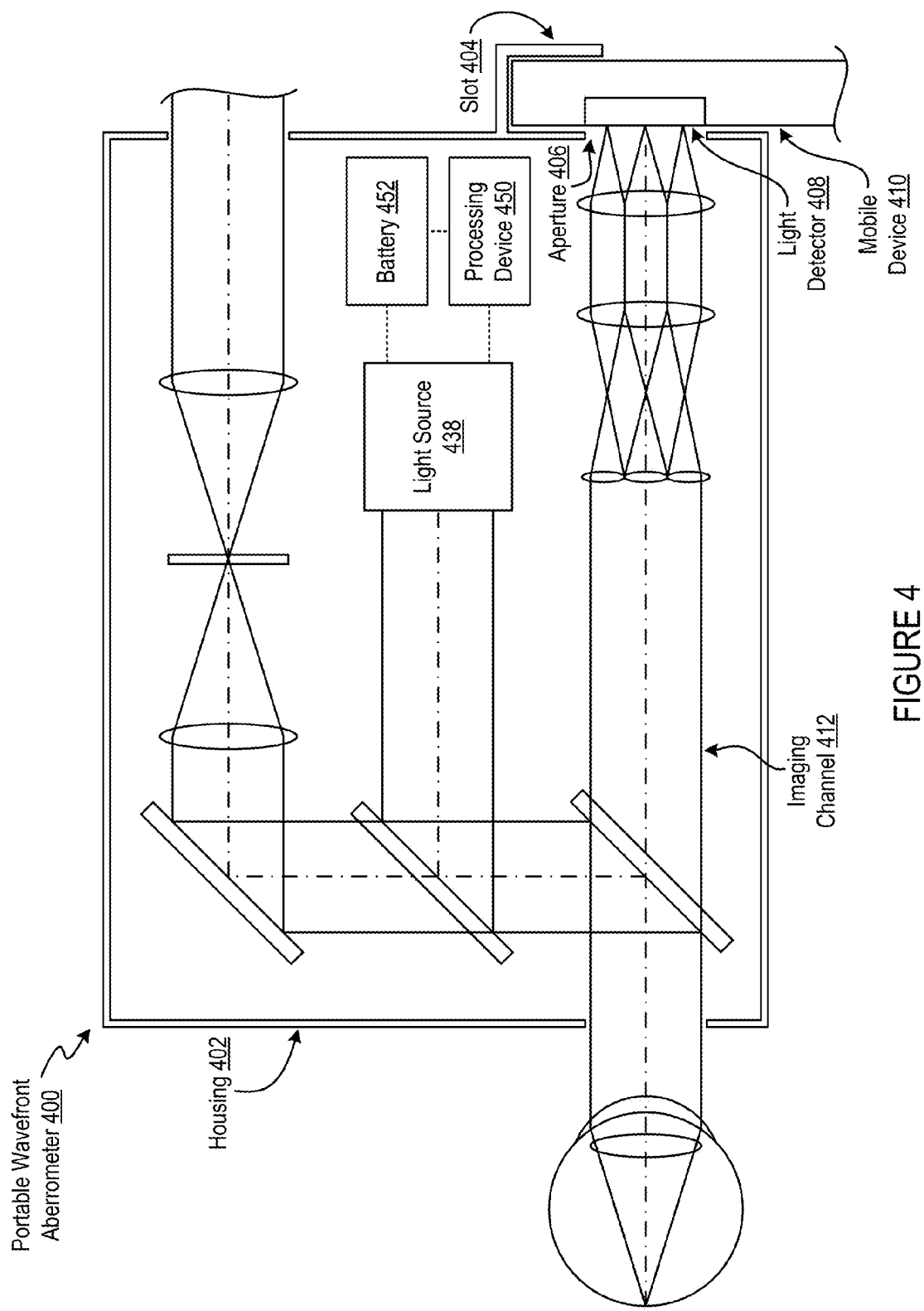
FIG. 4 is a schematic illustration of a portable wavefront aberrometer according to another embodiment of the present disclosure.
Figure 5:
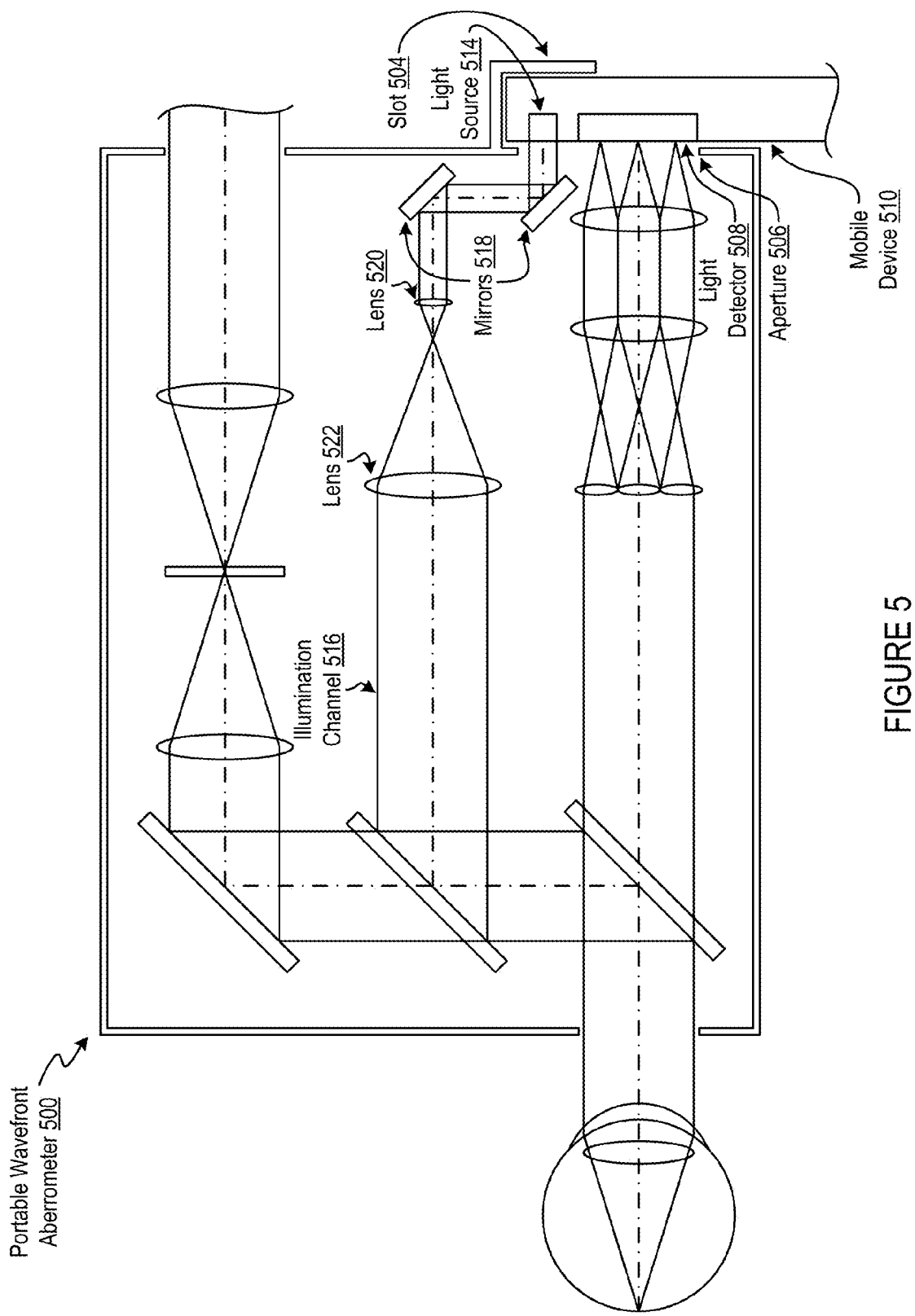
FIG. 5 is a schematic illustration of a portable wavefront aberrometer according to another embodiment of the present disclosure.

FIGS. 2E and 2F illustrate another embodiment of an optical device module 250. The optical components of the optical device module 250 are contained within a housing, which may have the form of a cylindrical shaft 252. The shaft 252 includes an eye cup 254 at a proximal end 256 (the "patient end"), and at least one aperture at a distal end 258 (the "device end"). The distal end 258 includes a plate 260 and a connector 262 for reversibly coupling the optical device module 250 to a mobile device 270. When the optical device module 250 is coupled to the mobile device 270, the plate 260 abuts the mobile device 270 while the connector 262 maintains the mobile device 270 in a position relative to the optical device module 250 such that a light detector 272 and/or light source 274 of the mobile device 270 are aligned with the optical components contained within the shaft 252. Additional connectors may also be used. In certain embodiments, the connector 262 is in a form of a sleeve or slot, as illustrated in FIGS. 4 and 5. In certain embodiments, the light source 274 of the mobile device 270 is used to illuminate the patient's eye during use. In other embodiments, an internal light source (e.g., light sources 338 or 438), such as a laser, may be disposed within the shaft 252 and may be used to generate light in lieu of the light source 274. In such embodiments, the shaft 252 may include an accessible battery compartment that can hold a battery (e.g., batteries 352 or 452) that is adapted to power the internal light source. In certain embodiments, the internal light source may be powered by the mobile device 270 via a physical connection made between the optical device module 250 and the mobile device 270.

Open Field Alignment Channel Embodiments

Certain embodiments of the present disclosure utilize an open field alignment channel that allows a patient to focus on an open field object during a vision examination. During the examination, the patient can see through the open field alignment channel and observe the object. The channel includes an alignment target (e.g., a transparent target with a visible crosshair) that allows the patient to aim for the object, which in turn aligns the patient's pupil with an optical imaging axis of the defined by the optical device. Moreover, having the patient focus on an object placed 4 or more meters away allows for focus relaxation and eliminates instrument-introduced myopia. While the following description of embodiments of an open field alignment channel is provided in the context of a portable wavefront aberrometer, it is noted that the embodiments are not limited as such. Embodiments of the open field alignment channel may be incorporated into other optical device embodiments described herein, such as a fundus camera or corneal topographer, as well as other optical devices not described herein.

Figure 3A:
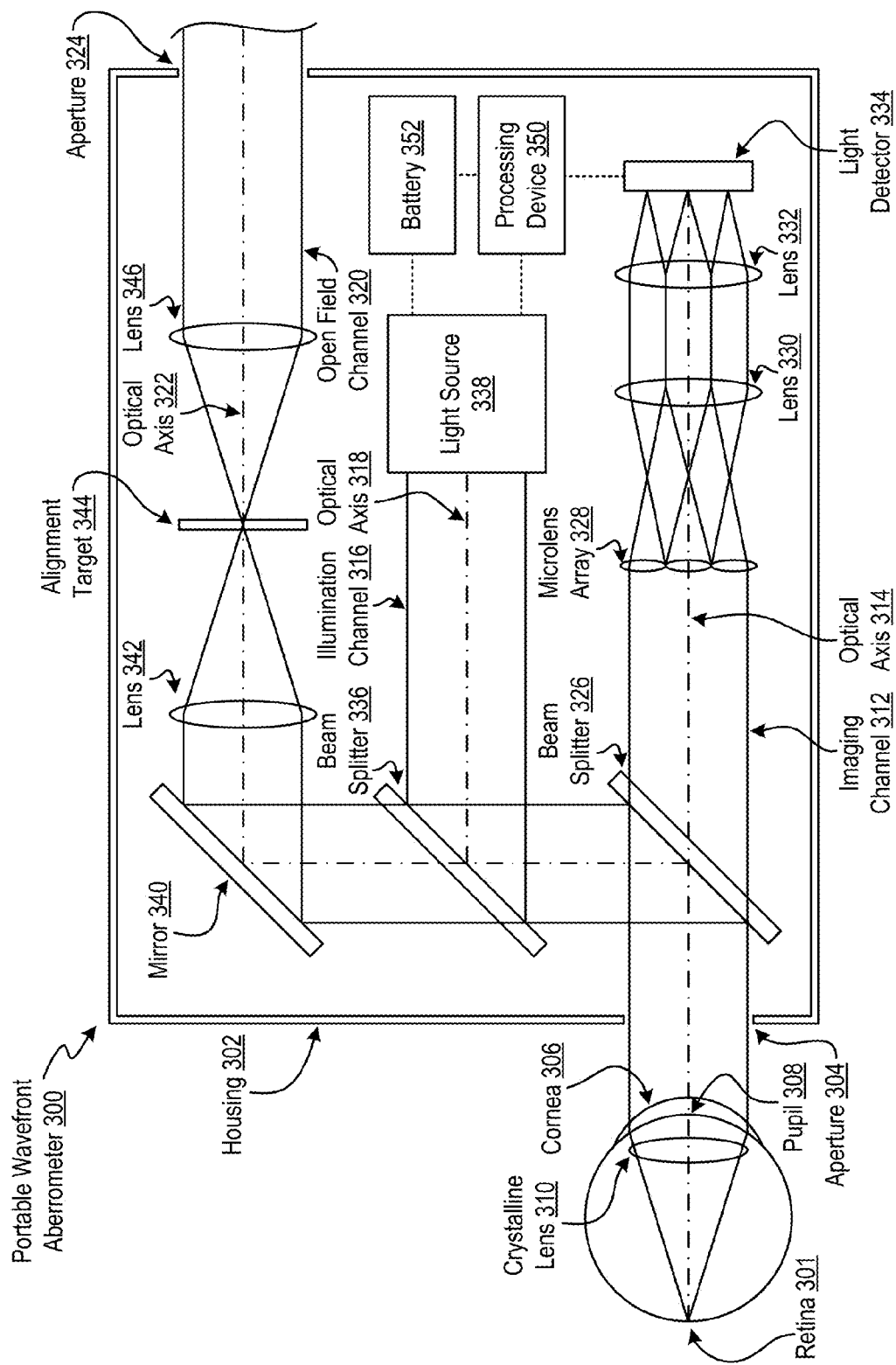
FIG. 3A is a schematic illustration of a portable wavefront aberrometer according to an embodiment of the present disclosure.

FIG. 3A is a schematic illustration of a portable wavefront aberrometer 300 according to an embodiment of the present disclosure. The portable wavefront aberrometer 300 includes a housing 302 that encloses a plurality of optical components, including lenses, beam splitters, and other components that define optical channels for directing light generated by a light source 338. The optical channels include an imaging channel 312, an illumination channel 316, and an open field channel 320. Collimated light from the illumination channel 316 is directed by beam splitters 336 and 326 through an aperture 304 of the housing 302 and to a patient's retina 301. The reflection and transmission ratios of the beam splitters 326 and 336 may be selected to allow a sufficient amount of light to be delivered to the eye, as would be appreciated by one of ordinary skill in the art. As light enters the pupil 308, it is focused onto the retina 301 by cornea 306 and crystalline lens 310. The collimated light is reflected off of the retina 301 and passes again through the crystalline lens 310 and cornea 306 as it exits the pupil 308. The reflected light (post-retinal light) passes through the aperture 304 and beam splitter 326, and is directed through the imaging channel 312 to light detector 334. In certain embodiments, the light detector 334 is a complementary metal-oxide-semiconductor (CMOS) device. In other embodiments, the light detector 334 is a charge-coupled device (CCD).

In certain embodiments, the beam splitter 326, microlens array 328, lens 330, and lens 332 define the imaging channel 312 along an optical axis 314. The microlens array 328 includes a plurality of lenses that split and transform the light into a two-dimensional array of individually focused spots (a "spot array") at the focal plane of the microlens array 328. The resulting spot array then passes through the lens 330 and the lens 332, which create a conjugate image plane of the spot array onto the light detector 334. The optical design of the portable wavefront aberrometer 300 may place the microlens array 328 within several tens of millimeters of the pupil 308, which places the distance within the Rayleigh range used in near field propagation to provide a reasonable measurement of aberration even if the microlens array 328 is not in the conjugate plane of the pupil 308. Such is described in Bauman, B. J., & Eisenbies, S. K. (2006), "Adaptive Optics System Assembly and Integration," in Porter, J., et al (Ed.), *Adaptive Optics for Vision Science: Principles, Practices, Design, and Applications*, Wiley-Interscience, pp 155-187, the disclosure of which is hereby incorporated by reference herein in its entirety.

Although the precision of the portable wavefront aberrometer 300 increases as the number of lenses within the microlens array 328 increases, increasing the number of lenses may decreases the dynamic range (the amplitude of the optical aberration) of the portable wavefront aberrometer 300. A lower dynamic range may prevent the portable wavefront aberrometer 300 from measuring large aberrations. The number of lenses may be further limited by the size of each microlens and the size of the light beam entering the microlens array 328. In certain embodiments, a diameter of the light beam that enters the microlens array 328 ranges from about 2 to about 5 millimeters, corresponding to the size of the patient's undilated pupil 308. The microlens array 328 may include between 5 and 25 lenses along an X-axis, and between 5 and 25 lenses along a Y-axis (with the X- and Y-axes defining a plane that is normal to the optical axis 314). In certain embodiments, the number of lenses along the X-axis of the array is the same as the number of lenses along the Y-axis.

In certain embodiments, the light source 338 and the beam splitter 336 define an illumination channel 316 having an optical axis 318. In certain embodiments, one or more lenses may be included in the illumination channel 316. For example, a pair of lenses may be used to focus the generated light from the light source 338. In certain embodiments, the light source 338 may be a laser, such as a class 1 laser, or a light emitting diode (LED). In one embodiment, the light generated by the light source 338 may pass through an aperture stop to reduce a radius of the generated light beam. In one embodiment, a shutter may be utilized to block light from the light source 338 until a measurement is to be taken.

The light source 338 may be powered by a battery 352, which may be coupled to a battery port. The battery 352 may be a replaceable battery, such as an alkaline battery or lithium ion battery, and/or may include multiple batteries. In certain embodiments, the housing 302 may have a built-in port that allows for a connection to be made between the battery 352 and an external power source to recharge the battery 352. In certain embodiments, one or more indicator LEDs may be built into the housing 302 to serve as indicators of whether the battery 352 is currently being charged, whether the battery 352 is fully-charged, whether the battery 352 has low charge, and/or whether the portable wavefront aberrometer 300 is currently powered (either by the battery 352 or an external source).

The light source 338 may be of a sufficiently low power that prolonged exposure will not damage the patient's eye. This would allow for a user to turn on the light source 338 directly at the onset of the measurement and leave it on while one or more measurements are taken. In certain embodiments, the portable wavefront aberrometer 300 may include a toggle switch (e.g., located on an exterior portion of the housing 302) that would toggle power to the light source 338. In certain embodiments, a processing device 350 may be operatively coupled to the light source 338. The processing device 350 may be powered by the battery 352, and may activate or deactivate the light source 338, and/or control an amount of power supplied to the light source 338 by the battery 352. In certain embodiments, the processing device 350 may control a shutter and aperture stop of the light source 338. In certain embodiments, a signal sent from a mobile device (e.g., a Bluetooth or similar signal) may be received by the processing device 350, and the processing device 350 may activate the light source 338 in response. The processing device 350 may activate or deactivate the light detector 334, and receive image data generated by the light detector 334.

In certain embodiments, the portable wavefront aberrometer 300 may process image data of the eye captured by the light detector 334 using the processing device 350. The processing device 350 may be operatively coupled to a memory, which may be located within the housing 302. In other embodiments, the memory may be a portable memory device (e.g., a flash drive, a memory card, etc.) that can be inserted into a suitable port, for example, located within the housing 302 or integrally formed with the housing 302. In certain embodiments, the processing device 350 may transmit the captured image data to an external device via a network (e.g., via a network interface). The network may include a public network (e.g., the Internet), a private network (e.g., a local area network (LAN) or wide area network (WAN)), a wired network (e.g., Ethernet network), a wireless network (e.g., an 802.11 network, a Wi-Fi network, or a Bluetooth network), a cellular network (e.g., a Long Term Evolution (LTE) network), routers, hubs, switches, server computers, and/or a combination thereof. In certain embodiments, the network may include one or more networks operating as stand-alone networks or in cooperation with each other. The network may utilize one or more protocols of one or more devices to which it is communicatively coupled, and/or may have its protocols translated to one or more protocols of network devices.

In certain embodiments, a display device may be integrally formed in the housing 302. The display device may be operatively coupled to the processing device 350, which may cause the display device to display image data captured by the light detector 334, as well as processed/transformed data in certain embodiments.

While FIG. 3A depicts a single processing device 350, it is to be understood that other electronic components may be incorporated into the portable wavefront aberrometer 300, such as memories, input/output devices, network interfaces, etc. (e.g., some or all of the components of computer system 2500 described later with respect to FIG. 25).

Figure 3B:
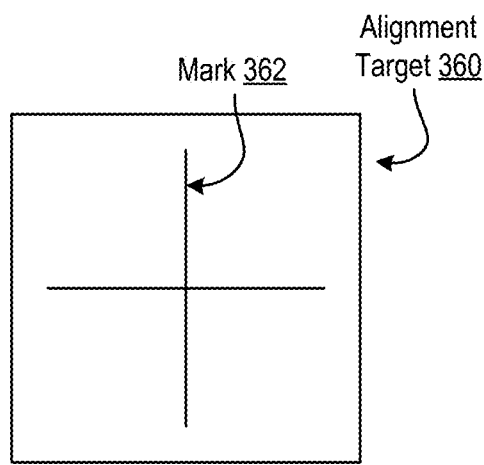
FIG. 3B depicts a square-shaped alignment target according to an embodiment of the present disclosure.
Figure 3C:
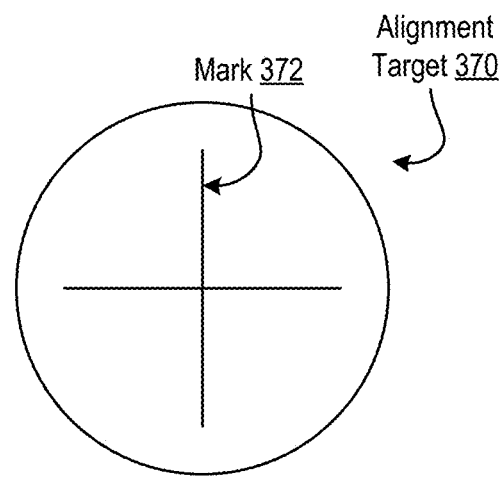
FIG. 3C depicts a circle-shaped alignment target according to an embodiment of the present disclosure.
Figure 3D:
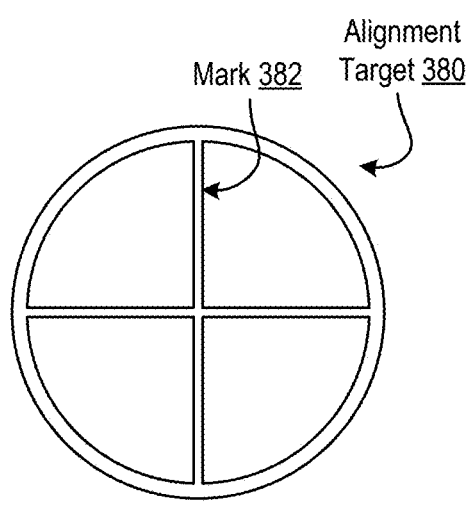
FIG. 3D depicts a hollow frame alignment target according to an embodiment of the present disclosure.

In certain embodiments, mirror 340, lens 342, alignment target 344, and lens 346 may define the open field channel 320 along an optical axis 322. The open field channel 320 may be defined to direct light into the housing 302 via an aperture 324 formed through the housing 302. The light may include one or more of reflected light, ambient light, or direct light produced by an external source. During a vision examination, the open field channel 320 allows a patient to focus on an "open field object" located a distance from the portable wavefront aberrometer 300. The open field object, for example, may be at least 4 meters away from the portable wavefront aberrometer 300 to facilitate eye focus relaxation. The alignment target 344 may act as a reticle that allows the patient to visually aim for the open field object, which may help align the pupil 308 along optical axis 314. This allows a patient to operate the portable wavefront aberrometer 300 and obtain useful data without requiring a medical practitioner or technician to determine if the patient's pupil 308 is properly aligned. In certain embodiments, the alignment target 344 is located at a focal point of the open field channel 320. In certain embodiments, the alignment target 344 is a transparent or semi-transparent disc having a non-transparent mark formed thereon, such as a targeting reticle, a point, arrows, or any other mark that facilitates aiming. FIG. 3B illustrates a square-shaped alignment target 360 having a cross-shaped mark 362. FIG. 3C illustrates a circle-shaped alignment target 370 having a cross-shaped mark 372. Any suitable shape may be used for the alignment target 344. In certain embodiments, the alignment target 344 may be a hollow frame with a mark being formed as a freestanding structure (e.g., an "X" or cross formed by two struts spanning a ring-shaped frame). FIG. 3D illustrates a hollow-frame alignment target 380 with a cross-shaped mark 382 formed as a freestanding structure. The alignment target 344 may be arranged such that the mark is centered on the optical axis 322 of the open field channel 320. In certain embodiments, the alignment target 344 is removable, and may be removed or absent entirely from the portable wavefront aberrometer 300.

It is to be understood that the components of the portable wavefront aberrometer 300 are merely illustrative, and that less than all of the components shown, as well as additional optical components, may be included while maintaining similar functionality. Other configurations and layouts may be used, as would be appreciated by one of ordinary skill in the art. Moreover, various features of the portable wavefront aberrometer 300 described above are not limited to portable wavefront aberrometers per se, and could be implemented in any of the embodiments described below as would be appreciated by one of ordinary skill in the art.

FIG. 4 is a schematic illustration of a portable wavefront aberrometer 400 according to an embodiment of the present disclosure. The portable wavefront aberrometer 400 differs from the portable wavefront aberrometer 300 in terms of how the reflected light is captured. Specifically, the light detector 334 of portable wavefront aberrometer 300 is omitted and is replaced by a light detector 408 (e.g., a camera) of a mobile device 410. It is noted also that light source 438, processing device 450, and battery 452 may be the same or similar to their identically named counterparts of FIG. 3A. The mobile device 410 may be mechanically coupled to a slot 404 (or by any other suitable mechanical coupling/connector) that positions the light detector 408 over an aperture 406 to allow light to be directed by an imaging channel 412 to the light detector 408. The optical components defining the imaging channel 412 may be similar to those defining the imaging channel 312 except that the components are re-arranged to accommodate the location of the light detector 408. In certain embodiments, the light source 438 may be controlled by the mobile device 410. For example, the mobile device 410 may communicate with the processing device 450 via a wireless or wired connection, which in turn controls the light source 438.

In the embodiment illustrated in FIG. 4, the housing 402 and its components serve as a module that, when coupled to the mobile device 410, collectively define the portable wavefront aberrometer 400. FIG. 5 illustrates a variation of the embodiment illustrated in FIG. 4, in which a portable wavefront aberrometer 500 utilizes light generated by a light source 514 of a mobile device 510. The mobile device 510 may be coupled to a slot 504 (or by any other suitable mechanical coupling/connector) that positions the light detector 508 over an aperture 506 to allow light generated by the light source 514 to be directed by an illumination channel 516 to the patient's eye. Reflected light may be directed back through the aperture 506 to the light detector 508. Mirrors 518, lens 520, and lens 522 may direct and focus the generated light beam along the illumination channel 516.

Figure 6:
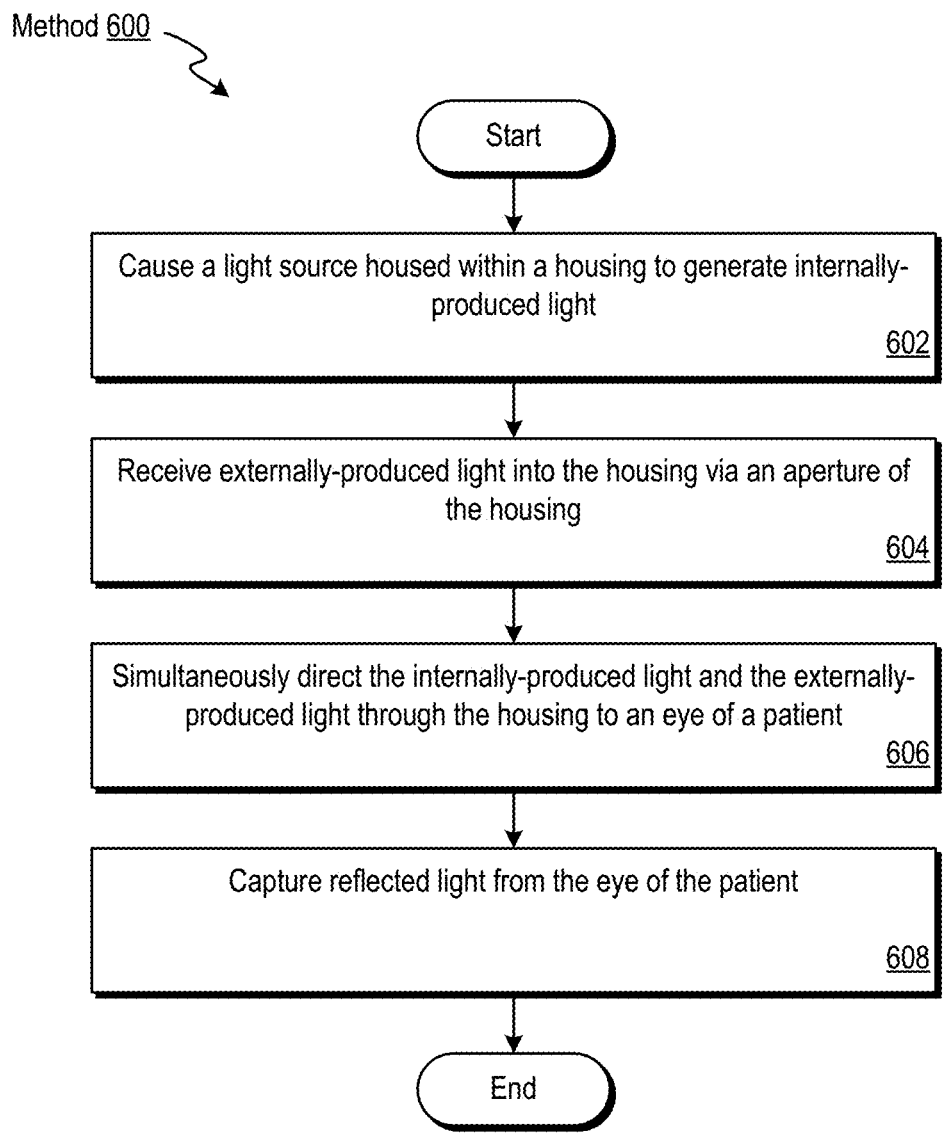
FIG. 6 is a block diagram illustrating a method for performing a diagnostic test on a patient's eye according to an embodiment of the present disclosure.

FIG. 6 is a block diagram illustrating a method 600 for performing a diagnostic test on a patient's eye according to an embodiment of the present disclosure. For example, method 600 may be performed using the portable wavefront aberrometer 300 described with respect to FIG. 3A.

At block 602, a light source (e.g., light source 338) within a housing (e.g., housing 302) generates internally-produced light. The internally-produced light may be generated in response to a processing device (e.g., processing device 350) activating the light source or in response to manual activation of the light source by a patient, medical practitioner, or technician (e.g., by pressing a button or a switch).

At block 604, externally-produced light is received into the housing via an aperture (e.g., aperture 324) of the housing. In certain embodiments, the externally-produced light comprises light reflected off of an object located at least 4 meters from the aperture of the housing.

At block 606, the internally-produced light and the externally-produced light are simultaneously directed through the housing to an eye of the patient. In certain embodiments, the externally-produced light is directed through an alignment target (e.g., alignment target 344) disposed within the housing prior to the externally-produced light reaching the eye of the patient.

At block 608, reflected light from the eye of the patient is captured by a light detector (e.g., light detector 334). In certain embodiments, the reflected light is directed through a microlens array (e.g., microlens array 328) prior to being captured by the light detector. In certain embodiments, an image of the captured light is transmitted (e.g., via the processing device, such as processing device 350) to a remote device that computes a patient-specific parameter comprising on or more of a Snellen fraction, a measurement of an optical aberration, or an eyeglasses prescription. In certain embodiments, the image of the captured light may include a fundus image of the eye or a corneal topography map. In certain embodiments, the captured light is processed by the processing device within the housing.

Portable Fundus Camera Embodiments

Certain embodiments of the present disclosure relate to a portable fundus camera. A fundus camera module may be reversibly attached to a mobile device, such as a smartphone, personal digital assistant, laptop, or palmtop computer to utilize a light detector (e.g., camera) and/or light source of the mobile device. In certain embodiments, the fundus camera module may be coupled to a peripheral camera (e.g., a webcam), which is coupled to another device for processing. The fundus camera module may include a connector for connecting the module to the mobile device, such as a slot, sleeve, adhesive, clip, clamp, or other suitable material or structure for reversibly coupling the module to the mobile device. In certain embodiments, the fundus camera is a self-contained device.

Traditional fundus cameras are typically large and lack portability, with units having a footprint of at least 1300 $cm^2$ and a mass of 20 kg or greater. Moreover, their costs often exceed $10,000. In contrast, the embodiments described herein provide increased portability and cost a fraction of a traditional tabletop fundus camera. In certain embodiments, the fundus camera may be modularized into a separate fundus camera module that forms a fully-functional unit when combined with a mobile device. The module and self-contained device are small enough to be stored in a cabinet drawer or carried in a pocket.

The resulting images obtained by a fundus camera embodiment described herein may be viewed by a medical practitioner, or sent to another individual's device. The data gathered by the camera may also be processed through algorithms known in the art by the mobile device's microcomputer/processing device, or the data may be transmitted by the mobile device to a different computer for processing. Such processing may allow for automated comparison to other such images or implementation as a slide in a presentation documenting changes the retina over time. In certain embodiments, light reflected onto the light detector may be presented to the medical practitioner as a picture or the patient's retina. This picture may be static, or it may be a video capture as desired by the medical practitioner. Software on the mobile device may also limit the information presented to the end user and send the unprocessed image, the processed image, and/or data extracted from the image to the medical practitioner. Fundus images acquired in accordance with the embodiments described herein are useful in the diagnosis and treatment of a number of ophthalmic conditions, including diabetic retinopathy, macular edema, aneurysms, and tracking of optic nerve degeneration.

Figure 7:
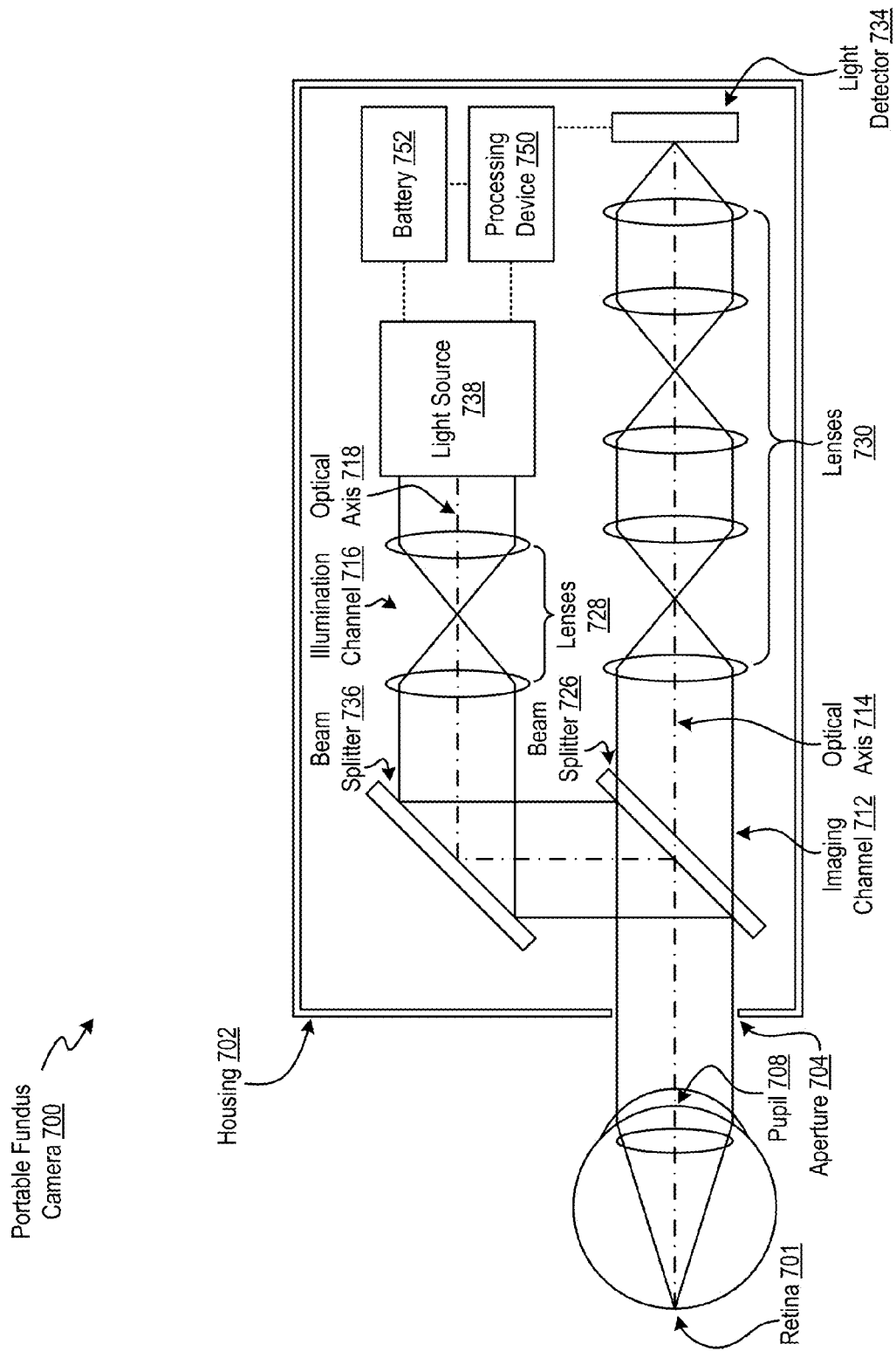
FIG. 7 is a schematic illustration of a portable fundus camera according to an embodiment of the present disclosure.

FIG. 7 is a schematic illustration of a portable fundus camera 700 according to an embodiment of the present disclosure. The portable fundus camera 700 includes a housing 702 that encloses a plurality of optical components, including lenses, beam splitters, and other components that define optical channels for directing light generated by a light source 738. The optical channels include an imaging channel 712 and an illumination channel 716. Collimated light from the illumination channel 716 is directed by beam splitters 736 and 726 through an aperture 704 of the housing 702 and to a patient's retina 701. The reflection and transmission ratios of the beam splitters 736 and 726 may be selected to allow a sufficient amount of light to be delivered to the retina, as would be appreciated by one of ordinary skill in the art. Post-retinal (reflected) light passes through the aperture 704 and beam splitter 726, and is directed through the imaging channel 712 to light detector 734. In certain embodiments, the light detector 734 is a complementary metal-oxide-semiconductor (CMOS) device. In other embodiments, the light detector 734 is a charge-coupled device (CCD).

In certain embodiments, the illumination channel 716 includes lenses 728, which produce a divergent light beam that can enter the patient's pupil 708 and illuminate the retina 701 in wide area. Lenses 730 may form an optical relay that projects a conjugate imaging plane of light reflected off of the retina 701 onto the light detector 734. Additional lenses may be included in the imaging channel 712 to focus or collimate the light as desired. In order to separate light entering the patient's eye from light reflected out of the patient's eye, the portable fundus camera 700 may either direct the light entering the eye so that it enters at an angle to optical axis 714, or the light beam may be transformed by appropriate lenses and filters into an o-ring or doughnut shape, which may illuminate the retina 701 directly. Light reflected off the retina 701 would then pass through the center of the light ring before passing through the lenses 730 and reaching the light detector 734.

In certain embodiments, the light source 738 is activated in response to a signal sent from a separate mobile computing device when initiated by the user. In certain embodiments, the portable fundus camera 700 includes a switch for toggling power to the light source 738 in response to a signal received by a processing device 750 from the mobile computing device, such as a Bluetooth signal. In certain embodiments, the switch may be triggered by the firing of the mobile device's flash. In other embodiments, the switch may be a mechanical switch integrated into the housing 702 that can be used to toggle power to the light source 738. Power to the light source 738 may be supplied by a battery 752, or the power may be drawn from the mobile computing device. The light source 738, battery 752, and processing device 750 may be the same or similar to their identically named counterparts of FIG. 3A.

Figure 8:
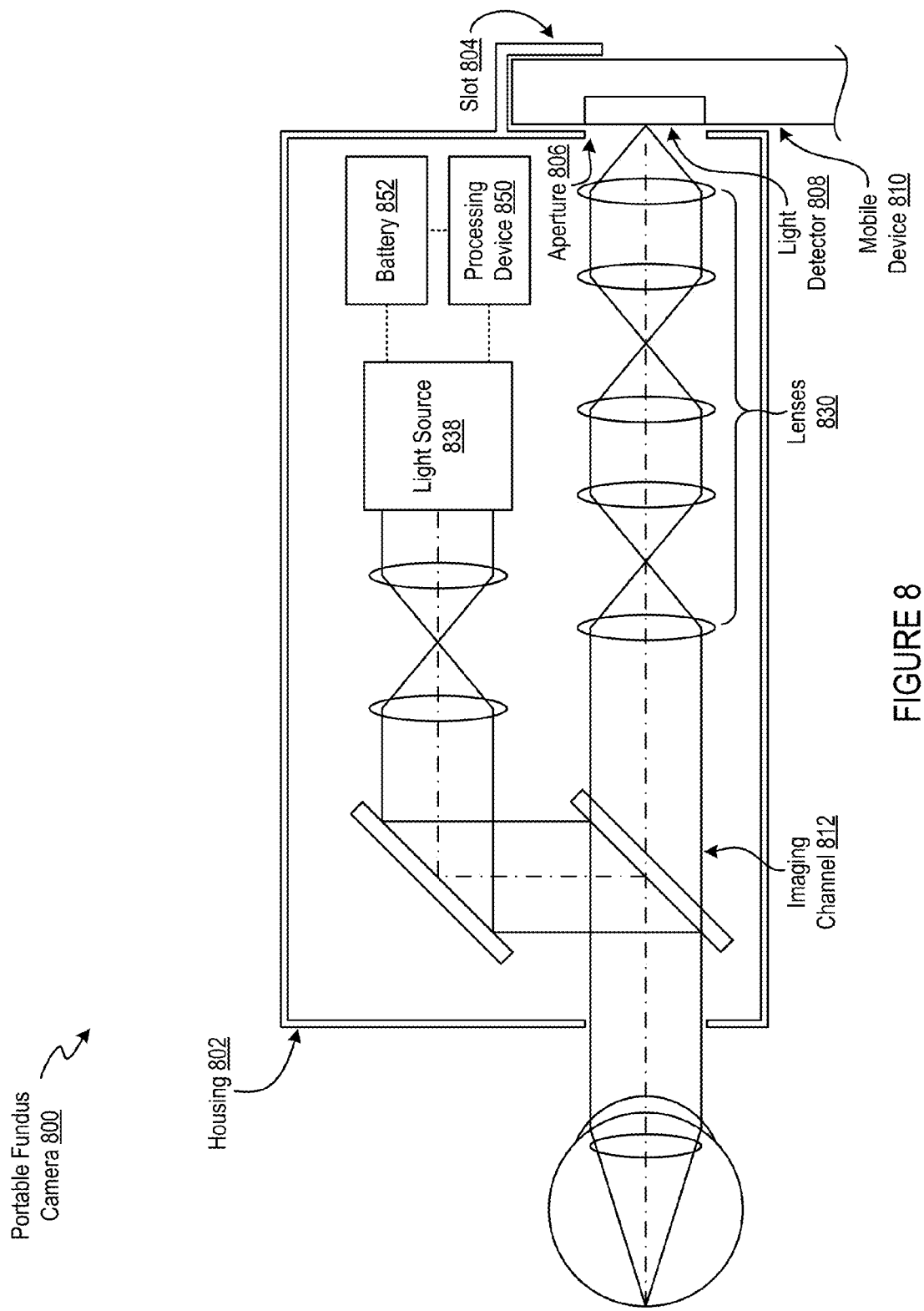
FIG. 8 is a schematic illustration of a portable fundus camera according to another embodiment of the present disclosure.

FIG. 8 is a schematic illustration of a portable fundus camera 800 according to an embodiment of the present disclosure. The portable fundus camera 800 differs from the portable fundus camera 700 in terms of how the reflected light is captured. Specifically, the light detector 734 of portable fundus camera 700 is omitted and is replaced by a light detector 808 (e.g., a camera) of a mobile device 810. It is noted also that light source 838, processing device 850, and battery 852 may be the same or similar to their identically named counterparts of FIG. 7. The mobile device 810 may be mechanically coupled to a slot 804 (or by any other suitable mechanical coupling/connector) that positions the light detector 808 over an aperture 806 to allow light to be directed by an imaging channel 812 to the light detector 808. The optical components defining the imaging channel 812 may be similar to those defining the imaging channel 712 except that the components (e.g., lenses 830) are re-arranged to accommodate the location of the light detector 808. In certain embodiments, the light source 838 may be controlled by the mobile device 810. For example, the mobile device 810 may communicate with the processing device 850 via a wireless or wired connection, which in turn controls the light source 838.

Figure 9:
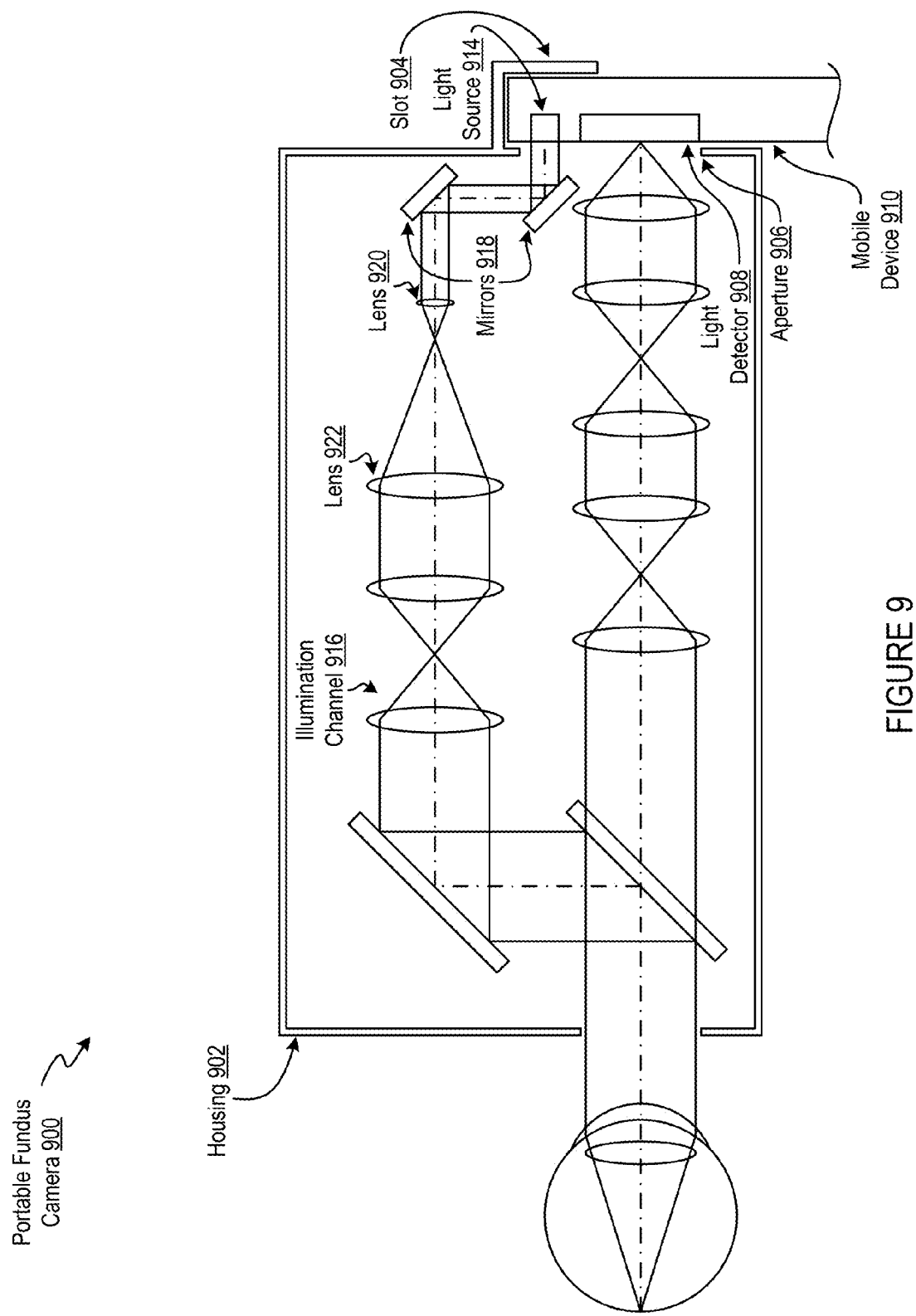
FIG. 9 is a schematic illustration of a portable fundus camera according to another embodiment of the present disclosure.

In the embodiment illustrated in FIG. 8, the housing 802 and its components serve as a module that, when coupled to the mobile device 810, collectively define the portable fundus camera 800. FIG. 9 illustrates a variation of the embodiment illustrated in FIG. 8, in which a portable fundus camera 900 utilizes light generated by a light source 914 of a mobile device 910. The mobile device 910 may be coupled to a slot 904 (or by any other suitable mechanical coupling/connector) that positions the light detector 908 over an aperture 906 of housing 902 to allow light generated by the light source 914 to be directed by an illumination channel 916 to the patient's eye. Reflected light may be directed back through the aperture 906 to the light detector 908. Mirrors 918, lens 920, and lens 922 may direct and focus the generated light beam along the illumination channel 916.

Figure 10:
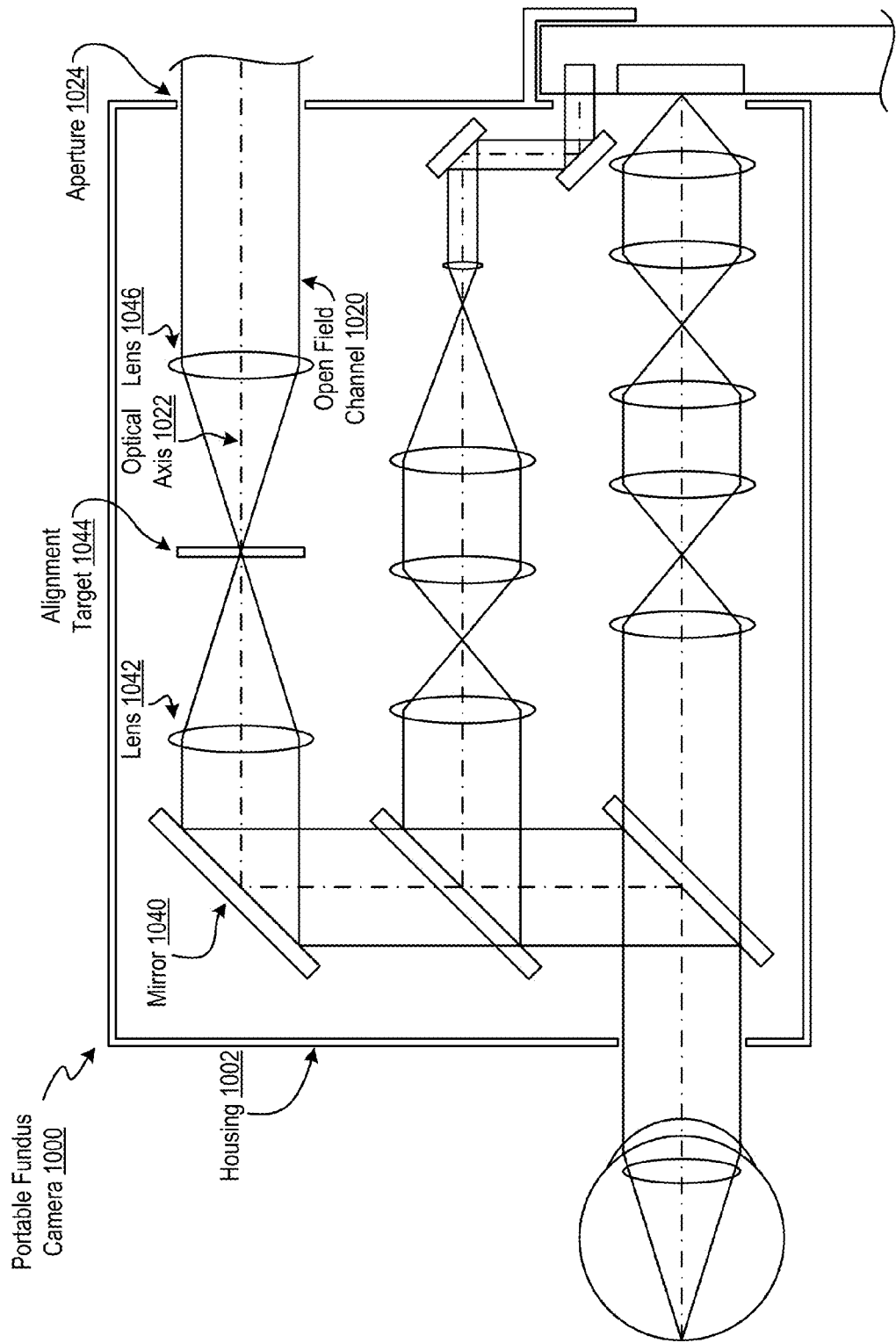
FIG. 10 is a schematic illustration of a portable fundus camera including an open field alignment channel according to an embodiment of the present disclosure.

FIG. 10 illustrates a variation of the portable fundus camera 900. Portable fundus camera 1000 includes an open field channel 1020, which may be the same or similar to its identically named counterpart of FIG. 3A. It is noted that the open field channel 1020 may be incorporated into other embodiments of a portable fundus camera, such as those described with respect to FIGS. 7 and 8, as would be appreciated by one of ordinary skill in the art. Portable fundus camera 1000 includes a mirror 1040, a lens 1042, an alignment target 1044, and a lens 1046, which collectively define the open field channel 1020 along an optical axis 1022. The open field channel 1020 may be defined to direct light into the housing 1002 via an aperture 1024 formed through the housing 1002.

Figure 11:
FIG. 11 is an example image of a patient's retina that may be captured by a portable fundus camera according to an embodiment of the present disclosure.

FIG. 11 is an example image of a patient's retina that may be captured by a portable fundus camera according to an embodiment of the present disclosure. The image captured by the light detector may be viewed by an administering medical practitioner, or may be transmitted to another device or individual. The image may be analyzed and compared to other images, either of the same retina or to a standard image as desired by the medical practitioner. In certain embodiments, the image may be transferred, either processed or unprocessed, to another computing device for remote access (e.g., telemedicine).

Figure 12:
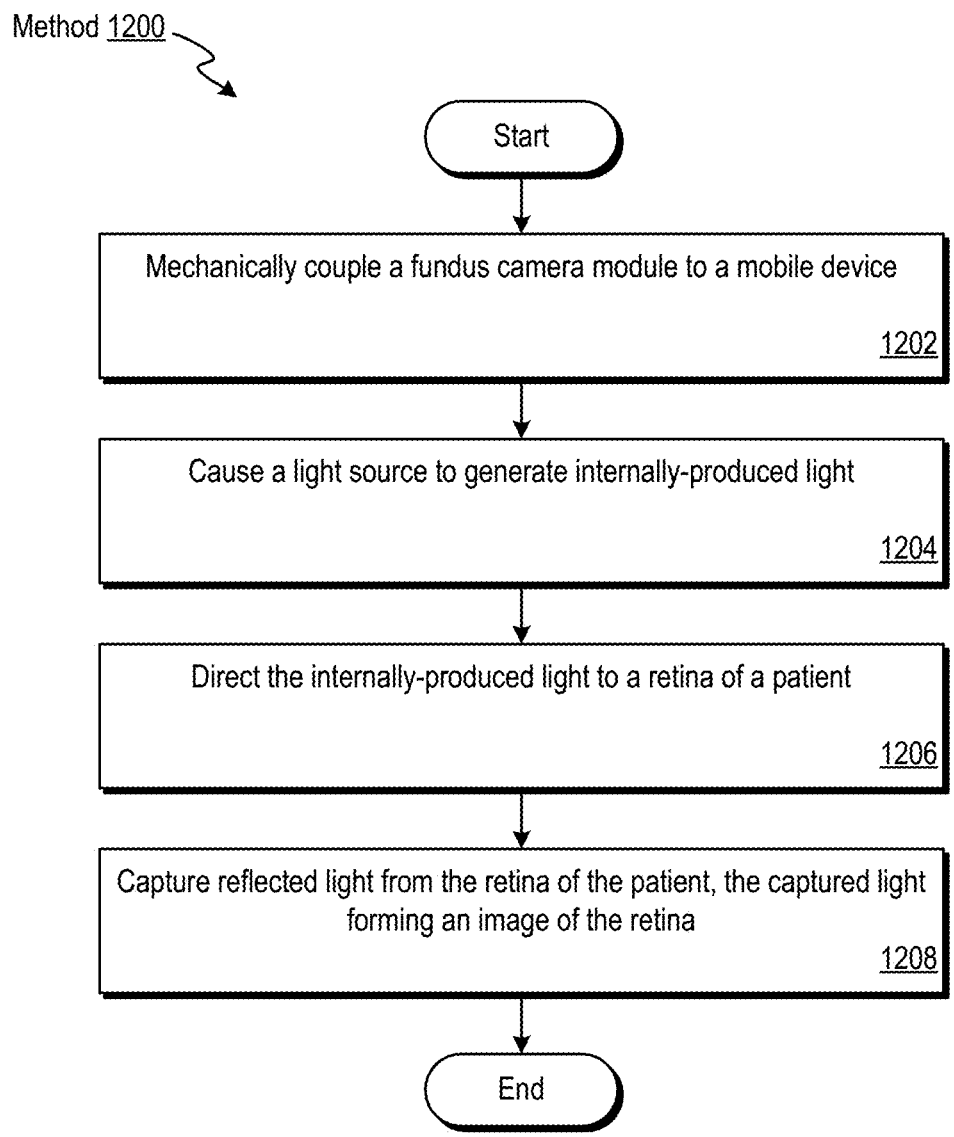
FIG. 12 is a block diagram illustrating a method for imaging a patient's retina according to an embodiment of the present disclosure.

FIG. 12 is a block diagram illustrating a method 1200 for imaging a patient's retina according to an embodiment of the present disclosure. For example, method 1200 and variants thereof may be performed using the portable fundus cameras 700, 800, 900, or 1000 described with respect to FIGS. 7-10.

At block 1202, a fundus camera module (e.g., illustrated as housing 802) is mechanically coupled to a mobile device (e.g., mobile device 810). In certain embodiments, a housing of the fundus camera module is in a form of an extended shaft having a proximal end and a distal end. The fundus camera module may include a connector (e.g., slot 804) located at the distal end of the extended shaft, with the fundus camera module being mechanically coupled to the mobile device via the connector. In certain embodiments, the connector includes a plate (e.g., plate 260) having a proximal surface and a distal surface, with the extended shaft (e.g., shaft 252) being a contiguous extension that extends proximally from the proximal surface of the plate. The distal end of the extended shaft defines an opening through the plate, and the distal surface of the plate abuts at least a portion of a surface of the mobile device.

In certain embodiments, block 1202 may be omitted, for example, when the portable fundus camera is a self-contained fundus camera (e.g., portable fundus camera 700).

At block 1204, a light source generates internally-produced light. In certain embodiments, the light source is contained within the housing (e.g., light sources 738 or 838). The internally-produced light may be generated in response to a processing device (e.g., processing devices 750 or 850) activating the light source or in response to manual activation of the light source by a patient, medical practitioner, or technician (e.g., by pressing a button or a switch). In certain embodiments, the light source is a light source of a mobile device (e.g., light source 914).

At block 1206, the internally-produced light is directed to a retina of a patient through the housing. In certain embodiments, the fundus camera is adapted to transform the internally-produced light into a ring-shaped light beam.

In certain embodiments, the portable fundus camera or portable fundus camera module may include an open field alignment channel (e.g., open field channel 1020). For example, externally-produced light may be received into the housing via an aperture of the housing (e.g., aperture 1024). The externally-produced light and the internally-produced light may be simultaneously directed through the housing and to the retina of the patient. In certain embodiments, the externally-produced light includes light reflected off of an object located at least 4 meters from the aperture of the housing. In certain embodiments, the externally-produced light is directed through an alignment target disposed within the housing prior to the externally-produced light reaching the retina of the patient. In certain embodiments, the alignment target includes a transparent disc having a non-transparent mark formed thereon.

At block 1208, reflected light from the retina of the patient is captured by a light detector (e.g., light detectors 734, 808, or 908), with the captured light forming an image of the retina. In certain embodiments, an image of the captured light is transmitted (e.g., via processing device 750) to a remote device for storage, processing, or analysis. In certain embodiments, the captured light is processed by the processing device within the housing or by a processing device of the mobile device. In certain embodiments that include an open field alignment channel, the reflected light corresponds to light reflected off of the retina of the patient as the patient is focusing on the object using the alignment target.

Portable Corneal Topographer Embodiments

Certain embodiments of the present disclosure relate to a portable corneal topographer for mapping the surface curvature of a cornea. Such mapping is useful for planning ophthalmic procedures such as cataract surgery, intraocular lens implantation, and refractive surgeries. It is also useful for evaluating the results of such procedures and in checking the fit of contact lenses. A corneal topographer module may be reversibly attached to a mobile device, such as a smartphone, personal digital assistant, laptop, or palmtop computer to utilize a light detector (e.g., camera) and/or light source of the mobile device. In certain embodiments, the corneal topographer camera module may be coupled to a peripheral camera (e.g., a webcam), which is coupled to another device for processing. The corneal topographer module may include a connector for connecting the module to the mobile device, such as a slot, sleeve, adhesive, clip, clamp, or other suitable material or structure for reversibly coupling the module to the mobile device. In certain embodiments, the corneal topographer is a self-contained device.

In certain embodiments, a corneal topographer may utilize wavefront sensing to map corneal shape. For example, a light source, such as a laser, housed within the corneal topographer or corneal topographer module may generate the light to be reflected from the eye. An internal processing device or a processing device of a mobile device may be used to process captured images.

Traditional corneal topographers are typically large and lack portability, with units having a footprint of at least 1200 $cm^2$ and a mass of 10 kg or greater. Moreover, their costs often exceed $10,000. In contrast, the embodiments described herein provide increased portability and cost a fraction of a traditional tabletop corneal topographer. Thus, because of the compact size and lower cost of the disclosed embodiments, medical practitioners in a practice could more easily afford their own portable corneal topographer and thereby increase the number of measurements or contact lens fittings per day.

Most corneal topographers operate by directing concentric rings of light onto a patient's cornea and capturing an image of the light reflected off of it. This image is then analyzed by a computer which displays a relevant topographical map to the practitioner. The data captured by the camera may then be processed through algorithms known in the art by a processing device, or the data may be transmitted to a remote device for processing. The data may be presented to the end user in an unprocessed form or as a corneal topogram. Certain embodiments of the present disclosure avoid directing concentric rings of light onto the patient's cornea. In certain embodiments, the light directed toward the patient's cornea may be of sufficient diameter to cover the patient's entire pupil. Light may be reflected from the surface of the pupil as well as from the retina, while the intensity of the light reflected from the cornea is greater than that of light reflected from the retina. Retinal-reflected light may be useful in some instances, but could confound a corneal map. No additional structures, such as a pinhole aperture to block corneal-reflected light, are used in such embodiments.

Figure 13:
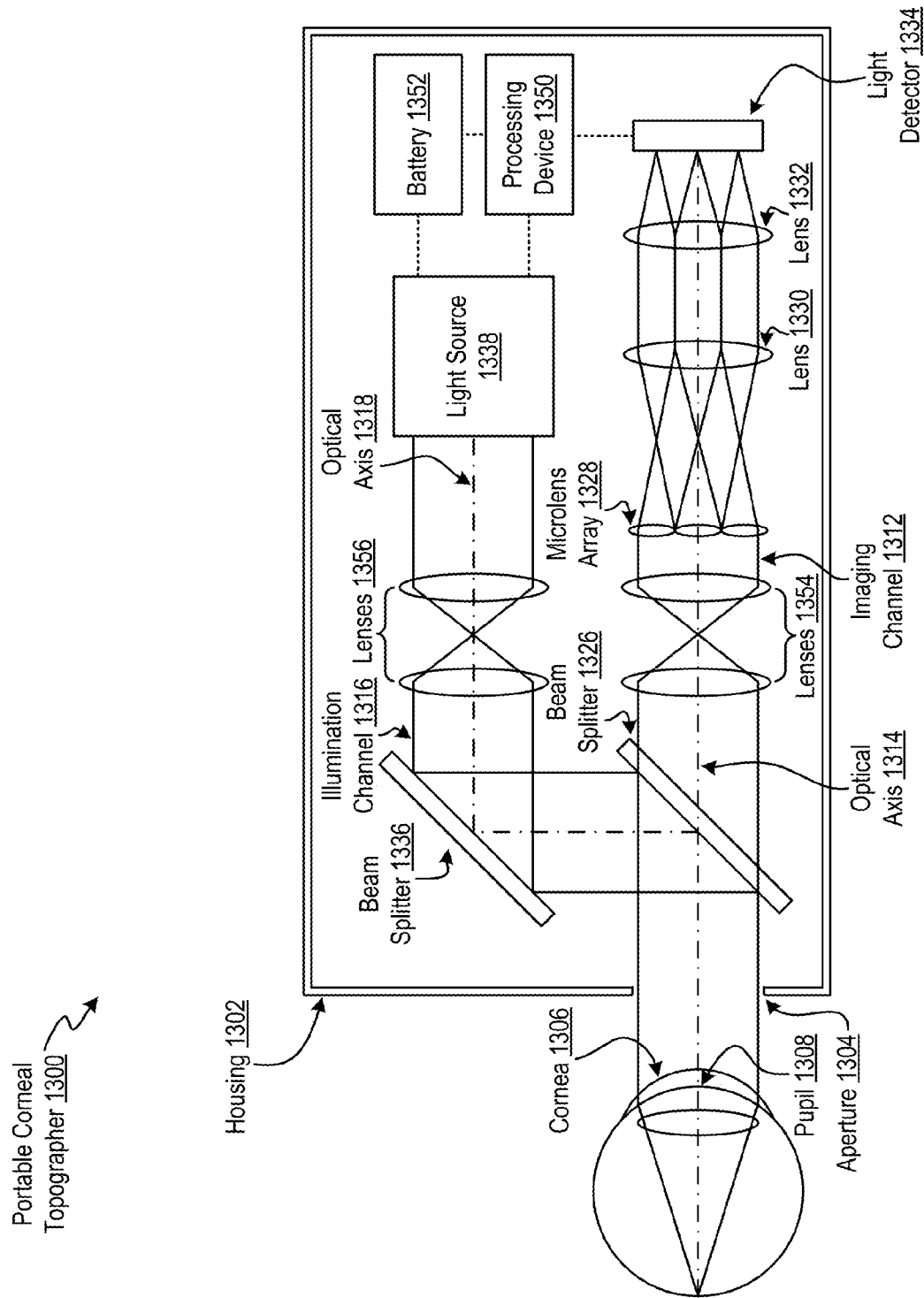
FIG. 13 is a schematic illustration of a portable corneal topographer according to an embodiment of the present disclosure.

FIG. 13 is a schematic illustration of a portable corneal topographer 1300 according to an embodiment of the present disclosure. The portable corneal topographer 1300 includes a housing 1302 that encloses a plurality of optical components, including lenses, beam splitters, and other components that define optical channels for directing light generated by a light source 1338. The optical channels include an imaging channel 1312 and an illumination channel 1316. Collimated light from the illumination channel 1316 is directed by beam splitters 1336 and 1326 through an aperture 1304 of the housing 1302 and to a patient's cornea 1306. The reflection and transmission ratios of the beam splitters 1336 and 1326 may be selected to allow a sufficient amount of light to be delivered to the eye, as would be appreciated by one of ordinary skill in the art. Reflected light passes through the aperture 1304 and beam splitter 1326, and is directed through the imaging channel 1312 to light detector 1334. In certain embodiments, the light detector 1334 is a complementary metal-oxide-semiconductor (CMOS) device. In other embodiments, the light detector 1334 is a charge-coupled device (CCD).

Additional lenses may be located in between the light source 1338 and the patient's cornea 1306, between the patient's cornea 1306 and the microlens array 1328, and between the microlens array 1328 and the light detector 1334 to focus or collimate the light as desired. For example, in certain embodiments, the light reflected from the cornea 1306 passes through lenses 1354, which form a telescope lens pair to create an image plane of the cornea 1306 which is then separated by the microlens array 1328. In certain embodiments, light generated by the light source 1338 passes through lenses 1356 to adjust the diameter of the light beam and collimate the light beam. In certain embodiments, the diameter of the generated light beam is adjusted to a sufficient diameter that is greater than or equal to a diameter of the cornea 1306. For example, in certain embodiments, the light beam diameter is at least 9 millimeters, corresponding to the largest typical pupil size. In other embodiments, the diameter may be less than 9 millimeters, or may range from 9 millimeters to 12 millimeters.

In certain embodiments, the microlens array 1328 may include between 5 and 25 lenses along an X-axis, and between 5 and 25 lenses along a Y-axis. Although the precision of the portable corneal topographer 1300 increases as the number of lenses in the microlens array 1328 increases, this is an asymptotic relationship rather than a linear one. Such increases in array density above a certain point do not appreciably increase the instrument's precision. Accordingly, in certain embodiments, a total number of lenses ranges from 25 to 400.

In certain embodiments, the light source 1338 is activated in response to a signal sent from a separate mobile computing device when initiated by the user. In certain embodiments, the portable corneal topographer 1300 includes a switch for toggling power to the light source 1338 in response to a signal received by a processing device 1350 from the mobile computing device, such as a Bluetooth signal. In certain embodiments, the switch may be triggered by the firing of the mobile device's flash. In other embodiments, the switch may be a mechanical switch integrated into the housing 1302 that can be used to toggle power to the light source 1338. Power to the light source 1338 may be supplied by a battery 1352, or the power may be drawn from the mobile computing device. The light source 1338, battery 1352, and processing device 1350 may be the same or similar to their identically named counterparts of FIG. 3A.

Figure 14:
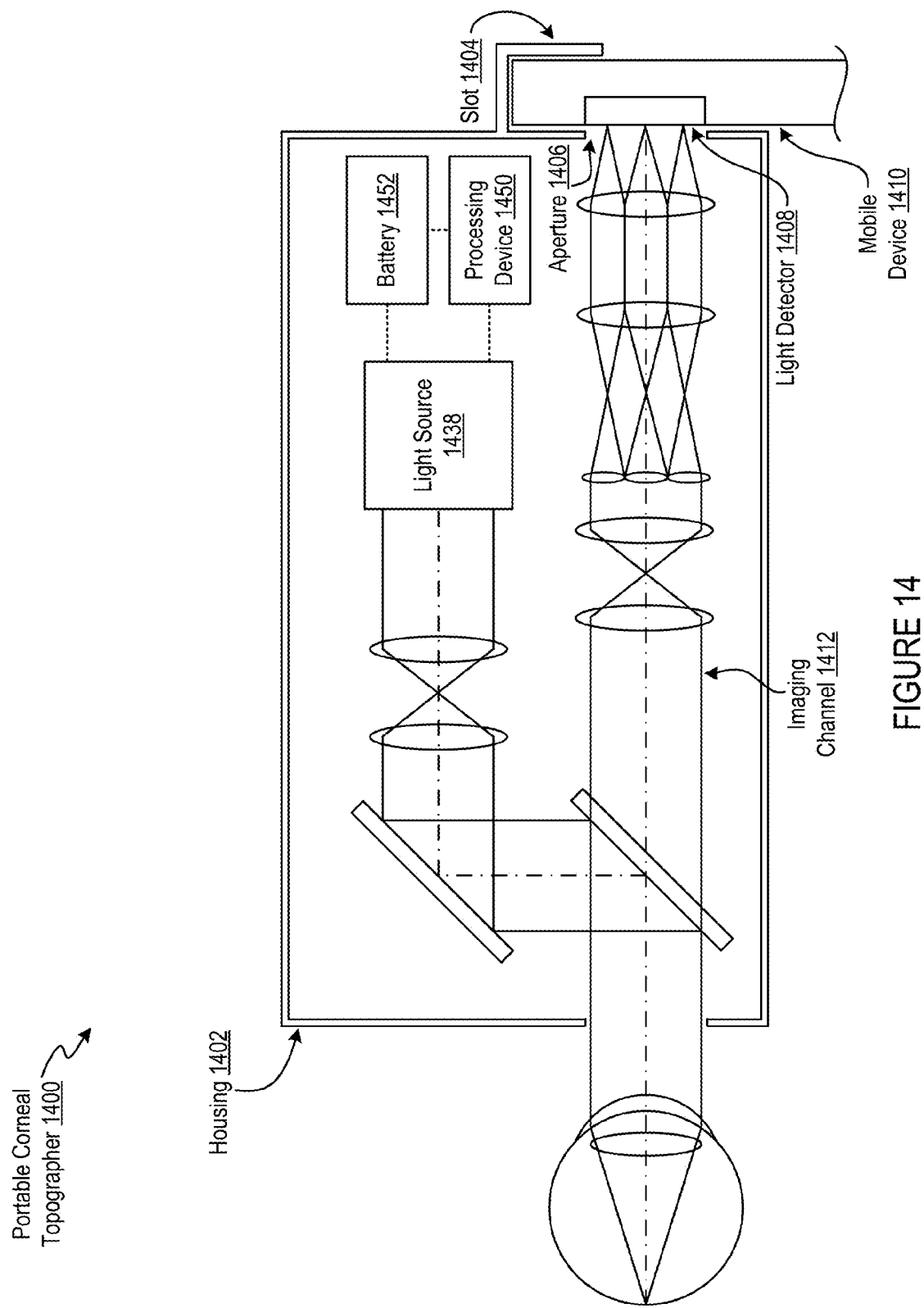
FIG. 14 is a schematic illustration of a portable corneal topographer according to another embodiment of the present disclosure.

FIG. 14 is a schematic illustration of a portable corneal topographer 1400 according to an embodiment of the present disclosure. The portable corneal topographer 1400 differs from the portable corneal topographer 1300 in terms of how the reflected light is captured. Specifically, the light detector 1334 of portable corneal topographer 1300 is omitted and is replaced by a light detector 1408 (e.g., a camera) of a mobile device 1410. It is noted also that light source 1438, processing device 1450, and battery 1452 may be the same or similar to their identically named counterparts of FIG. 13. The mobile device 1410 may be mechanically coupled to a slot 1404 (or by any other suitable mechanical coupling/connector) that positions the light detector 1408 over an aperture 1406 to allow light to be directed by an imaging channel 1412 to the light detector 1408. The optical components defining the imaging channel 1412 may be similar to those defining the imaging channel 1312 except that the components are re-arranged to accommodate the location of the light detector 1408. In certain embodiments, the light source 1438 may be controlled by the mobile device 1410. For example, the mobile device 1410 may communicate with the processing device 1450 via a wireless or wired connection, which in turn controls the light source 1438.

Figure 15:
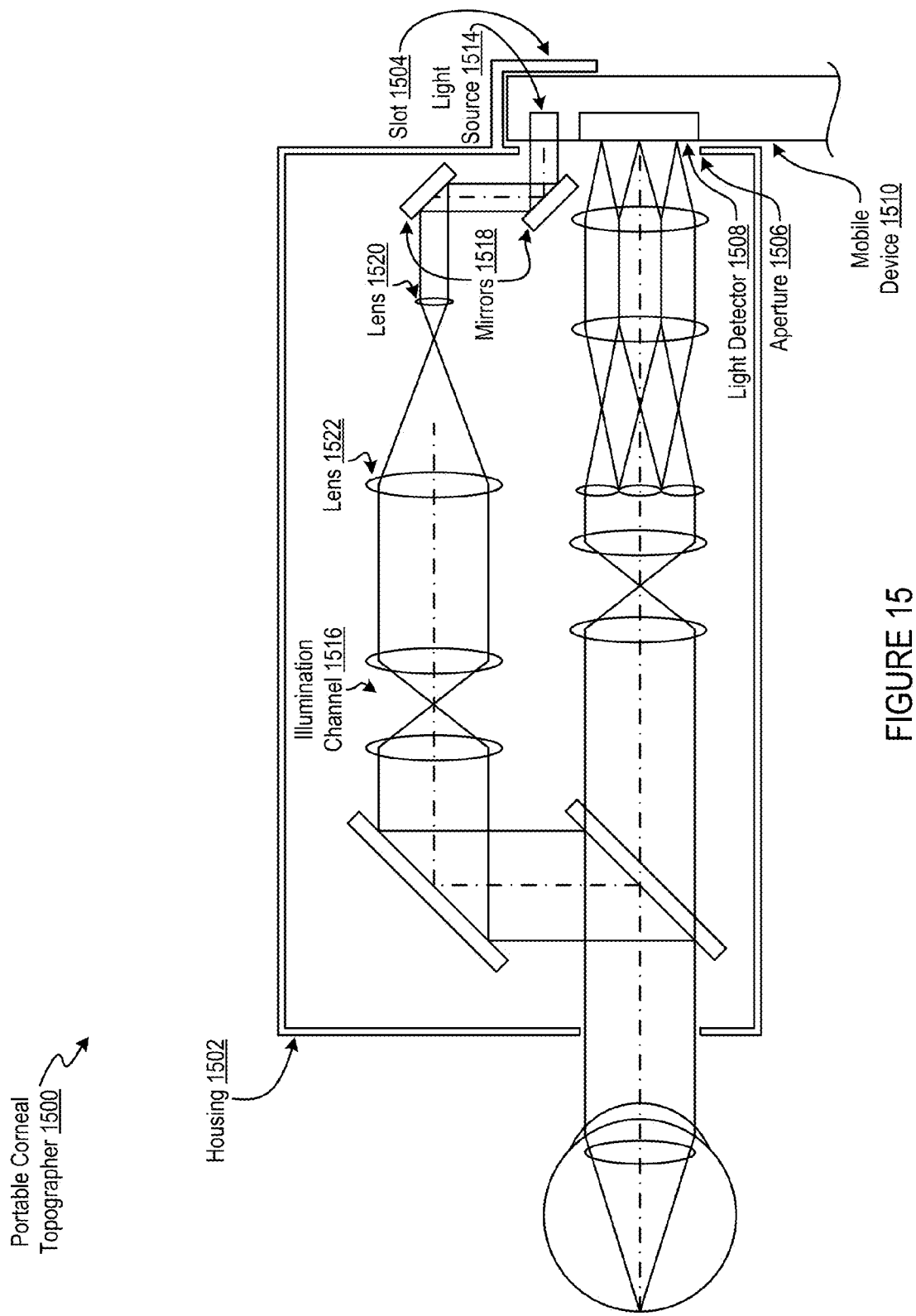
FIG. 15 is a schematic illustration of a portable corneal topographer according to another embodiment of the present disclosure.

In the embodiment illustrated in FIG. 14, the housing 1402 and its components serve as a module that, when coupled to the mobile device 1410, collectively define the portable corneal topographer 1400. FIG. 15 illustrates a variation of the embodiment illustrated in FIG. 14, in which a portable corneal topographer 1500 utilizes light generated by a light source 1514 of a mobile device 1510. The mobile device 1510 may be coupled to a slot 1504 (or by any other suitable mechanical coupling/connector) that positions the light detector 1508 over an aperture 1506 to allow light generated by the light source 1514 to be directed by an illumination channel 1516 to the patient's eye. Reflected light may be directed back through the aperture 1506 to the light detector 1508. Mirrors 1518, lens 1520, and lens 1522 may direct and focus the generated light beam along the illumination channel 1516.

Figure 16:
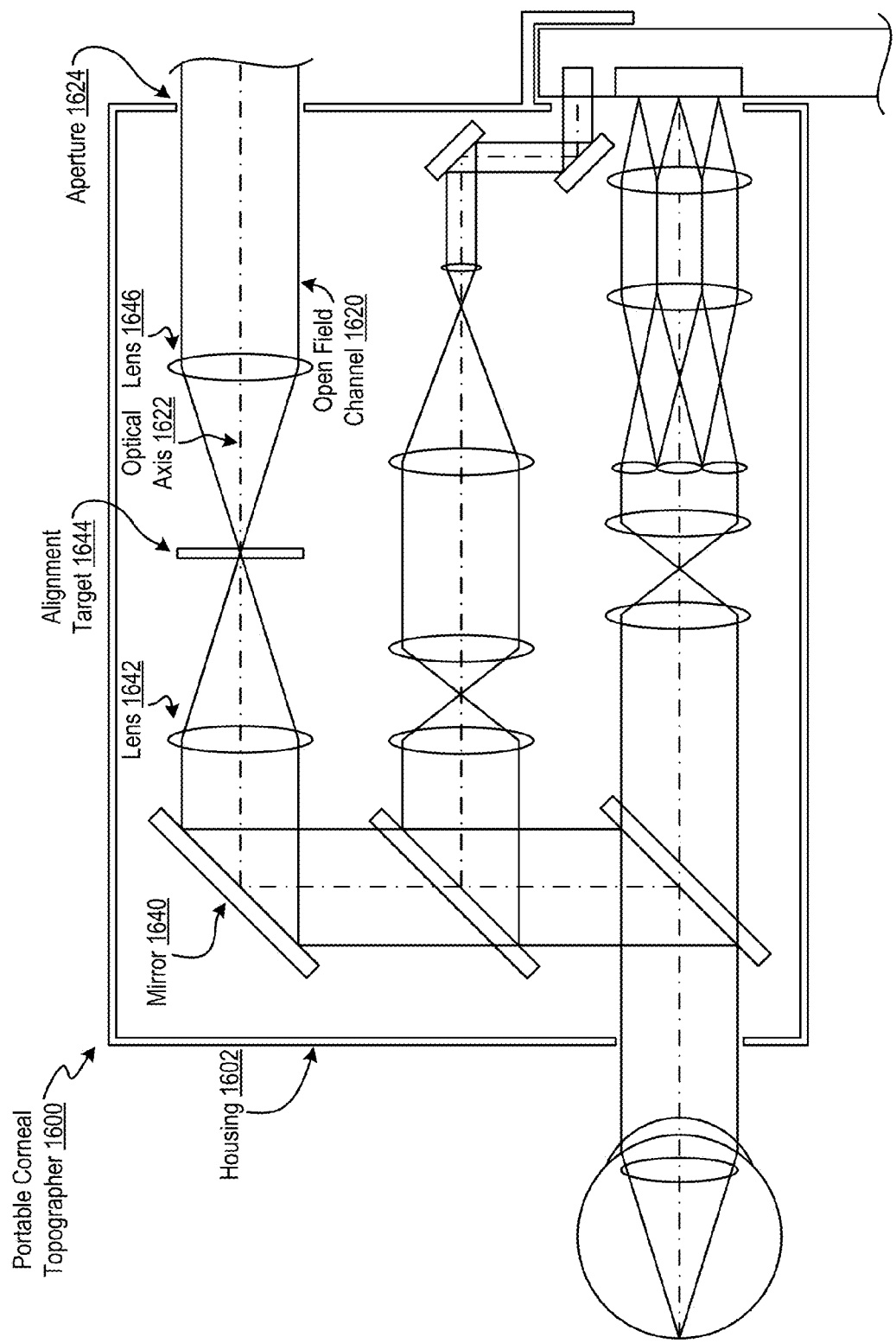
FIG. 16 is a schematic illustration of a portable corneal topographer including an open field alignment channel according to an embodiment of the present disclosure.

FIG. 16 illustrates a variation of the portable corneal topographer 1500. Portable corneal topographer 1600 includes an open field channel 1620, which may be the same or similar to its identically named counterpart of FIG. 3A. It is noted that the open field alignment channel may be incorporated into other embodiments of a portable corneal topographer, such as those described with respect to FIGS. 13 and 14, as would be appreciated by one of ordinary skill in the art. Portable corneal topographer 1600 includes a mirror 1640, a lens 1642, an alignment target 1644, and a lens 1646, which collectively define the open field channel 1620 along an optical axis 1622. The open field channel 1620 may be defined to direct light into the housing 1602 via an aperture 1624 formed through the housing 1602.

Figure 17:
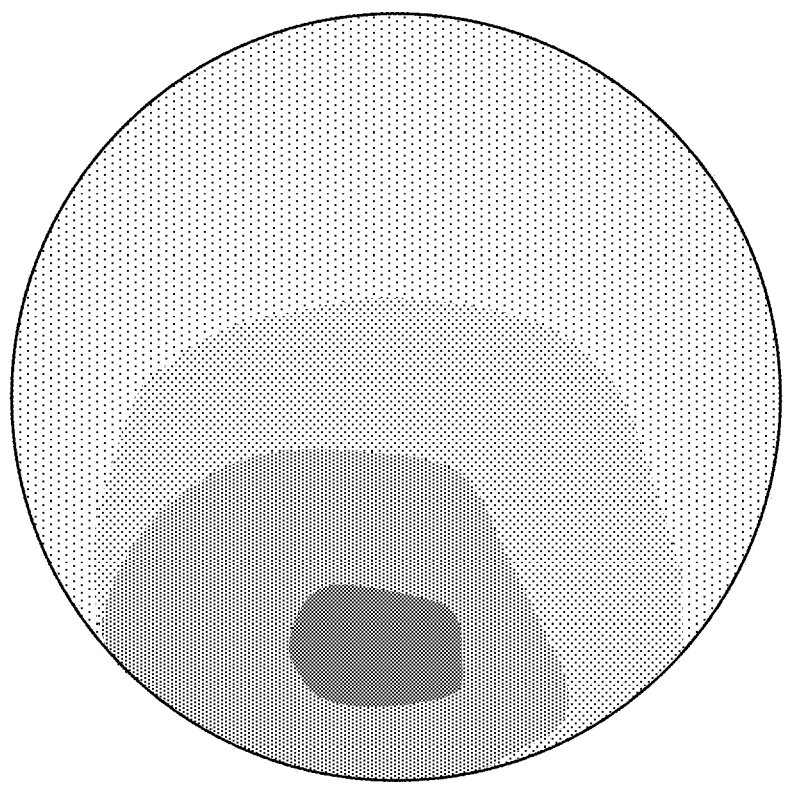
FIG. 17 illustrates an example of a corneal topographic map resulting from a transformation of the data acquired in accordance with an embodiment of the present disclosure.

FIG. 17 illustrates an example of a corneal topographic map resulting from a transformation of the data acquired in accordance with an embodiment of the present disclosure. Image data captured by a light detector may be processed by software implemented by a processing device of a self-contained corneal topographer, the mobile device, or a remote device to which the image data is transmitted. In certain embodiments, the software transforms the captured spot array image into a topographical map of the cornea.

Figure 18:
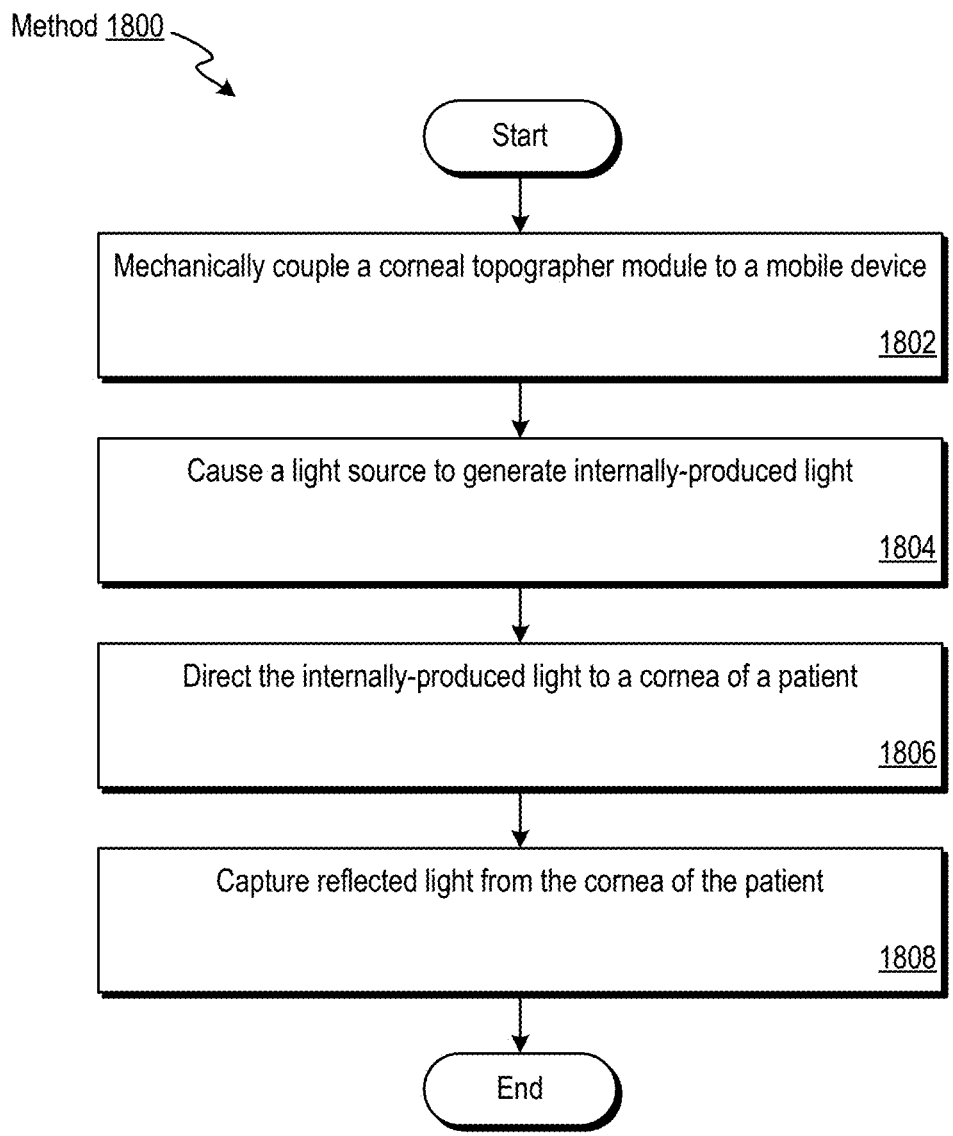
FIG. 18 is a block diagram illustrating a method for obtaining a corneal topography map according to an embodiment of the present disclosure.

FIG. 18 is a block diagram illustrating a method 1800 for obtaining a corneal topography map according to an embodiment of the present disclosure. For example, method 1800 and variants thereof may be performed using the portable corneal topographers 1300, 1400, 1500, or 1600 described with respect to FIGS. 13-16.

At block 1802, a corneal topographer module (e.g., illustrated as housing 1402) is mechanically coupled to a mobile device (e.g., mobile device 1410). In certain embodiments, a housing of the corneal topographer module is in a form of an extended shaft having a proximal end and a distal end. The corneal topographer module may include a connector (e.g., slot 1404) located at the distal end of the extended shaft, with the corneal topographer module being mechanically coupled to the mobile device via the connector. In certain embodiments, the connector includes a plate (e.g., plate 260) having a proximal surface and a distal surface, with the extended shaft (e.g., shaft 252) being a contiguous extension that extends proximally from the proximal surface of the plate. The distal end of the extended shaft defines an opening through the plate, and the distal surface of the plate abuts at least a portion of a surface of the mobile device.

In certain embodiments, block 1802 may be omitted, for example, when the portable corneal topographer is a self-contained corneal topographer (e.g., portable corneal topographer 1300).

At block 1804, a light source generates internally-produced light. In certain embodiments, the light source contained within the housing (e.g., light sources 1338 or 1438). The internally-produced light may be generated in response to a processing device (e.g., processing devices 1350 or 1450) activating the light source or in response to manual activation of the light source by a patient, medical practitioner, or technician (e.g., by pressing a button or a switch). In certain embodiments, the light source is a light source of a mobile device (e.g., light source 1514).

At block 1806, the internally-produced light is directed to a cornea of a patient through the housing. In certain embodiments, the portable corneal topographer or portable corneal topographer module may include an open field alignment channel (e.g., open field channel 1620). For example, externally-produced light may be received into the housing via an aperture of the housing (e.g., aperture 1624). The externally-produced light and the internally-produced light may be simultaneously directed through the housing and to the cornea of the patient. In certain embodiments, the externally-produced light includes light reflected off of an object located at least 4 meters from the aperture of the housing. In certain embodiments, the externally-produced light is directed through an alignment target disposed within the housing prior to the externally-produced light reaching the cornea of the patient. In certain embodiments, the alignment target includes a transparent disc having a non-transparent mark formed thereon.

At block 1808, reflected light from the cornea of the patient is captured by a light detector (e.g., light detectors 1334, 1408, or 1508). In certain embodiments, an image of the captured light is transmitted (e.g., via processing device 1350) to a remote device for storage, processing, or analysis. In certain embodiments, the captured light is processed by the processing device within the housing or by a processing device of the mobile device. In certain embodiments that include an open field alignment channel, the reflected light corresponds to light reflected off of the cornea of the patient as the patient is focusing on the object using the alignment target.

In certain embodiments, the reflected light is directed through a microlens array (e.g., microlens array 1328) prior to capturing the reflected light with the light detector. In certain embodiments, the microlens array includes a total number of lenses ranging from 25 to 400. In certain embodiments, the captured reflected light is transformed into a topographical image of the cornea, for example, by a processing device of the corneal topographer, corneal topographer module, mobile device, or remote device.

Portable Lensmeter Embodiments

Certain embodiments of the present disclosure relate to a portable lensmeter. Lensmeters are used to determine and verify the prescription of a lens. Lensmeters are useful for opticians during quality control procedures to ensure that a lens has been ground and polished within certain tolerances. Lensmeters are also useful in determining the prescription of a patient's current glasses before a refraction so that an optometrist or ophthalmologist can compare the new prescription and possibly glean clinically relevant information therefrom. During operation of a traditional lensmeter, a user first determines an optical center of the lens before manipulating a dial to bring each of two sets of lines into focus in order to determine the sphere and cylinder powers of the lens. Another manipulation determines the axis of the cylinder. These three numbers describe the majority of single-vision lenses. Multi-focal lenses, or lenses containing a prism correction, may also be measured by a lensmeter operator using similar techniques.

A lensmeter module, as described herein, may be reversibly attached to a mobile device, such as a smartphone, personal digital assistant, laptop, or palmtop computer to utilize a light detector (e.g., camera) and/or light source of the mobile device. In certain embodiments, the lensmeter module may be coupled to a peripheral camera (e.g., a webcam), which is coupled to another device for processing. The lensmeter module may include a connector for connecting the module to the mobile device, such as a slot, sleeve, adhesive, clip, clamp, or other suitable material or structure for reversibly coupling the module to the mobile device. In certain embodiments, a light source, such as a laser, housed within the lensmeter or lensmeter module may generate the light to be directed through a lens to be analyzed. An internal processing device or a processing device of a mobile device may be used to process captured images. In certain embodiments, the lensmeter is a self-contained device.

In certain embodiments, a lensmeter or lensmeter module may include an attachment site for holding a lens to be analyzed (e.g., a lens of a pair of glasses). A lens of a pair of glasses may be held in place by, for example, a slot formed in a housing of the lensmeter or lensmeter module. The embodiments described herein substantially eliminate the possibility of error on the part of the end user by minimizing user interaction from the operation of the instrument. In particular, the embodiments eliminate much of the instrumentation utilized by a traditional lensmeter so that the user does not have to manipulate dials to focus the images. Such measurements are less prone to user error, since the user's interaction with lensmeter and any associated computing device are minimal as compared to traditional lensmeters. A user need only place an unknown lens into a lens accepting region and activate the device. Captured light patterns for the lens can be compared to light patterns for known lenses or to light patterns generated by passing light through an empty path (e.g., when the light path does not include a lens to be measured).

In contrast to a traditional lensmeter, the disclosed embodiments are smaller, faster, and easier to use. Traditional lensmeters are typically large and lack portability, with units having a footprint of at least 800 cm$^2$ and a mass of 7 kg or greater. Moreover, their costs often exceed $4,000. In contrast, the embodiments described herein provide increased portability and cost a fraction of a traditional tabletop lensmeter. The embodiments are also more tolerant of lenses and internal reflective surfaces than traditional lensmeters. The exacting requirements of a traditional lensmeter require high quality lenses and careful calibration, however, the disclosed embodiments permit a manufacturer to use less expensive components and larger tolerances while maintaining high quality measurements due to the processing device's software being able to quickly calibrate measurements against a known lens or a blank.

Figure 19:
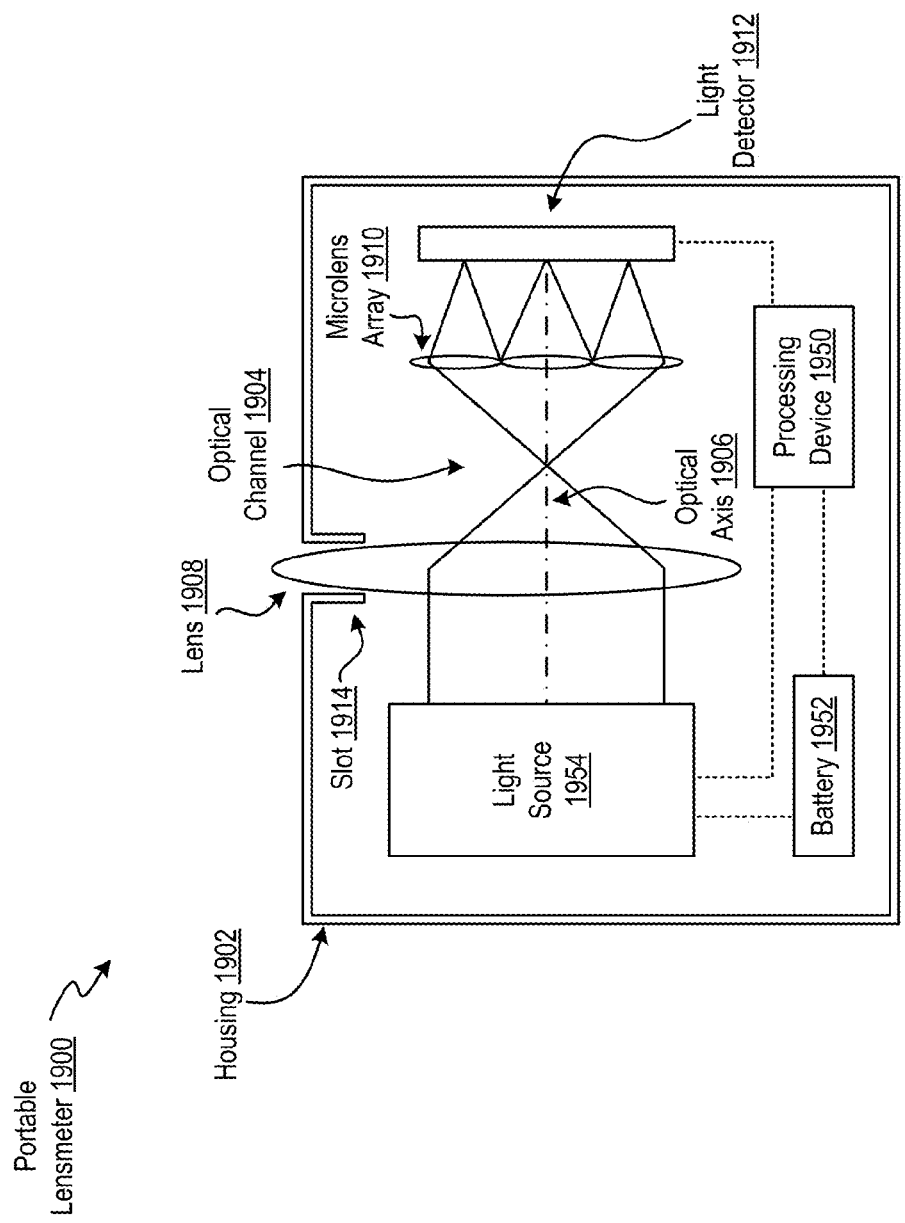
FIG. 19 is a schematic illustration of a portable lensmeter according to an embodiment of the present disclosure.

FIG. 19 is a schematic illustration of a portable lensmeter 1900 according to an embodiment of the present disclosure. The portable lensmeter 1900 includes a housing 1902 that encloses a plurality of optical components that define an optical channel 1904 for directing light generated by a light source 1954. Light generated by the light source 1954 passes through a lens 1908, through a microlens array 1910, and to a light detector 1912. In certain embodiments, the light detector 1912 is a complementary metal-oxide-semiconductor (CMOS) device. In other embodiments, the light detector 1912 is a charge-coupled device (CCD). Additional optical components may be utilized. For example, additional lenses may be located along the optical channel 1904 between the light source 1954 and the lens 1908, between the lens 1908 and the microlens array 1910, and/or between the microlens array 1910 and the light detector 1912 to focus or collimate the light as desired. One or more mirrors may be present in the optical channel 1904 to direct the light as desired, and may divert the light through other paths and optical channels. In certain embodiments, the housing 1902 includes a slot 1914 formed therein for receiving and reversibly coupling the lens 1908 to the housing 1902. The lens 1908 may be a lens of a pair of glasses, for example. The slot 1914 may serve as a guide for positioning the lens 1908 within the housing 1902 such that the lens is properly oriented with respect to the optical axis 1906 of the optical channel 1904.

In certain embodiments, a diameter of the light generated by the light source 1954 ranges from 2 to 6 millimeters, which may correspond to a size of a patient's undilated pupil. In certain embodiments, the microlens array 1910 may include between 5 and 25 lenses along an X-axis, and between 5 and 25 lenses along a Y-axis. Although the precision of the portable lensmeter 1900 increases as the number of lenses in the microlens array 1910 increases, this is an asymptotic relationship rather than a linear one. Such increases in array density above a certain point do not appreciably increase the instrument's precision. Accordingly, in certain embodiments, a total number of lenses ranges from 25 to 400.

In certain embodiments, the light source 1954 is activated in response to a signal sent from a separate mobile computing device when initiated by the user. In certain embodiments, the portable lensmeter 1900 includes a switch for toggling power to the light source 1954 in response to a signal received by a processing device 1950 from the mobile computing device, such as a Bluetooth signal. In certain embodiments, the switch may be triggered by the firing of the mobile device's flash. In other embodiments, the switch may be a mechanical switch integrated into the housing 1902 that can be used to toggle power to the light source 1954. Power to the light source 1954 may be supplied by a battery 1952, or the power may be drawn from the mobile computing device. The light source 1954, battery 1952, and processing device 1950 may be the same or similar to their identically named counterparts of FIG. 3A.

Figure 20:
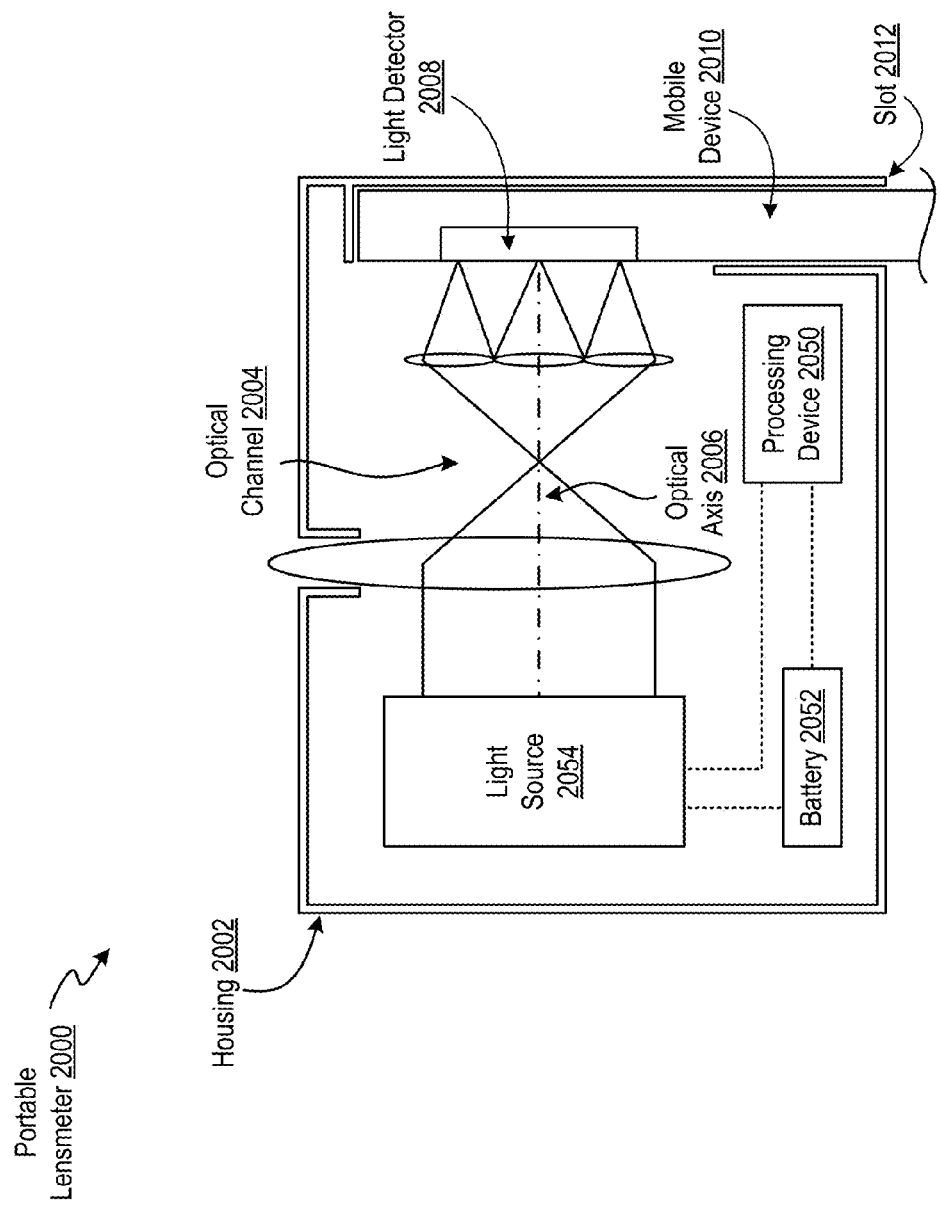
FIG. 20 is a schematic illustration of a portable lensmeter according to another embodiment of the present disclosure.

FIG. 20 is a schematic illustration of a portable lensmeter 2000 according to an embodiment of the present disclosure. The portable lensmeter 2000 differs from the portable lensmeter 1900 in terms of how the reflected light is captured. Specifically, the light detector 1912 of portable lensmeter 1900 is omitted and is replaced by a light detector 2008 (e.g., a camera) of a mobile device 2010. It is noted also that light source 2054, processing device 2050, and battery 2052 may be the same or similar to their identically named counterparts of FIG. 19. The mobile device 2010 may be mechanically coupled to a slot 2012 (or by any other suitable mechanical coupling/connector) that positions the light detector 2008 to allow light to be directed by an optical channel 2004 to the light detector 2008. The optical components defining the optical channel 2004 may be similar to those defining the optical channel 1904 but may be re-arranged to accommodate the location of the light detector 2008. In certain embodiments, the light source 2054 may be controlled by the mobile device 2010. For example, the mobile device 2010 may communicate with the processing device 2050 via a wireless or wired connection, which in turn controls the light source 2054.

Figure 21:
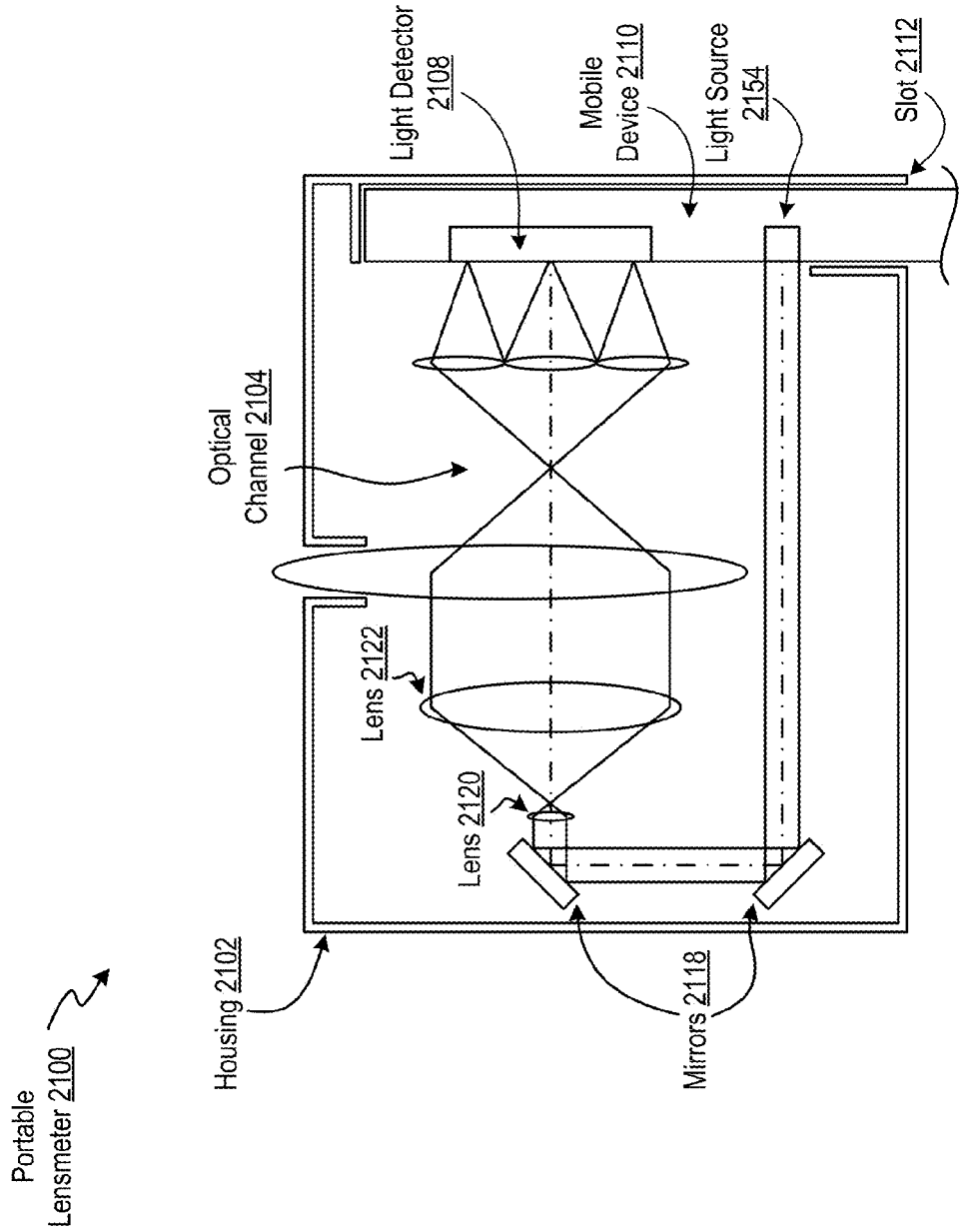
FIG. 21 is a schematic illustration of a portable lensmeter according to another embodiment of the present disclosure.

In the embodiment illustrated in FIG. 20, the housing 2002 and its components serve as a module that, when coupled to the mobile device 2010, collectively define the portable lensmeter 2000. FIG. 21 illustrates a variation of the embodiment illustrated in FIG. 20, in which a portable lensmeter 2100 utilizes light generated by a light source 2154 of a mobile device 2110. The mobile device 2110 may be coupled to a slot 2112 (or by any other suitable mechanical coupling/connector) that positions the light source 2154 to allow light generated by the light source 2154 to be directed along an optical channel 2104. Mirrors 2118, lens 2120, and lens 2122 may direct and focus the generated light beam along the optical channel 2104. Depending on the types, relative orientations, and sizes of the light detector 2108 and light source 2154, additional optical components may be utilized, for example, to direct, focus, and collimate the light beam.

Figure 22A:
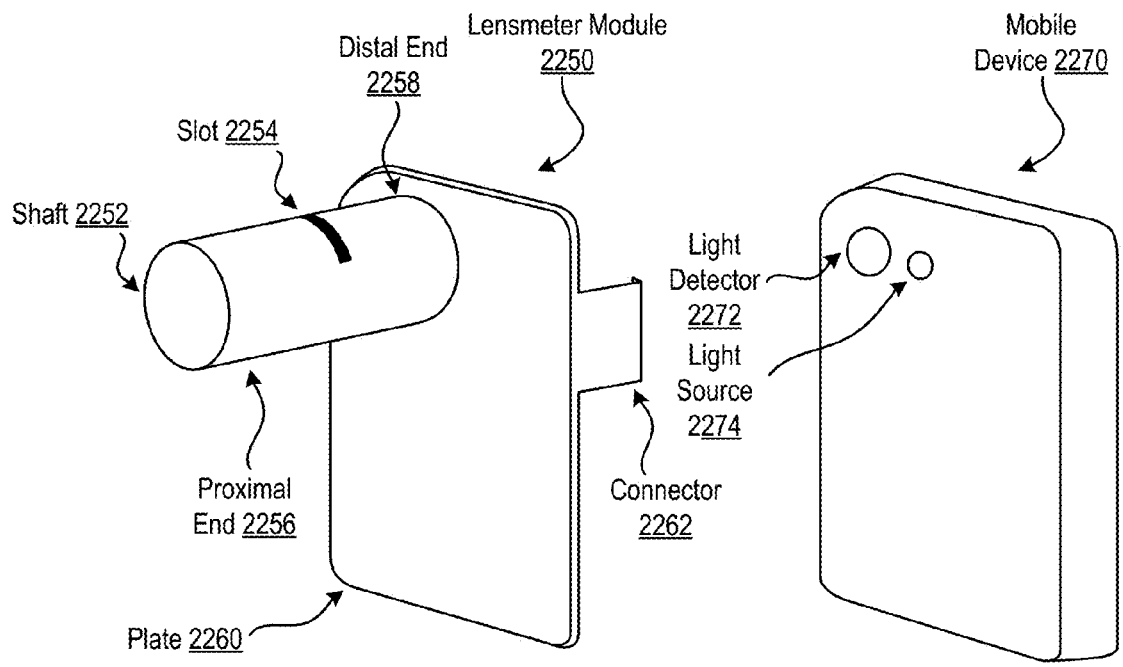
FIG. 22A is an illustration of an embodiment of a lensmeter module separated from a mobile device according to an embodiment of the present disclosure.
Figure 22B:
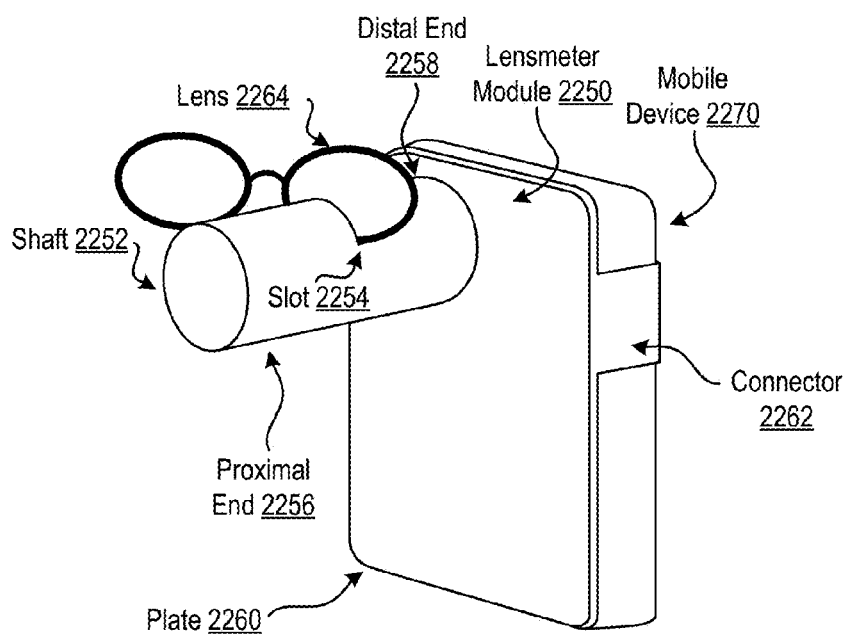
FIG. 22B is an illustration of an embodiment of lensmeter coupled to a lens and to a mobile device according to an embodiment of the present disclosure.

FIGS. 22A and 22B illustrate another embodiment of a lensmeter module 2250. The optical components of the module are contained within a housing, which may have the form of a cylindrical shaft 2252. The shaft 2252 has a proximal end 2256 and a distal end 2258 with at least one aperture formed in the shaft 2252 at the distal end 2258. The distal end 2258 includes a plate 2260 and a connector 2262 for reversibly coupling the lensmeter module 2250 to a mobile device 2270. When the lensmeter module 2250 is coupled to the mobile device 2270, the plate 2260 abuts the mobile device 2270 while the connector maintains the mobile device 2270 in a position relative to the lensmeter module 2250 such that a light detector 2272 and/or light source 2274 of the mobile device 2270 are aligned with the optical components contained within the shaft 2252. Additional connectors may also be used. In certain embodiments, the connector is in a form of a sleeve or slot, as illustrated in FIGS. 20 and 21. In certain embodiments, an internal light source (e.g., light sources 1954 or 2054), such as a laser, may be disposed within the shaft 2252. In such embodiments, the shaft 2252 may include an accessible battery compartment that can hold a battery (e.g., batteries 1952 or 2052) that is adapted to power the internal light source. In certain embodiments, the internal light source may be powered by the mobile device 2270 via a physical connection made between the lensmeter module 2250 and the mobile device 2270. A slot 2254 may be formed in the shaft 2252 (e.g., slot 1914 formed in housing 1902), which may be adapted for receiving and reversibly coupling a lens 2264. The lens 2264 may be a single lens of a pair of glasses.

Figure 23:
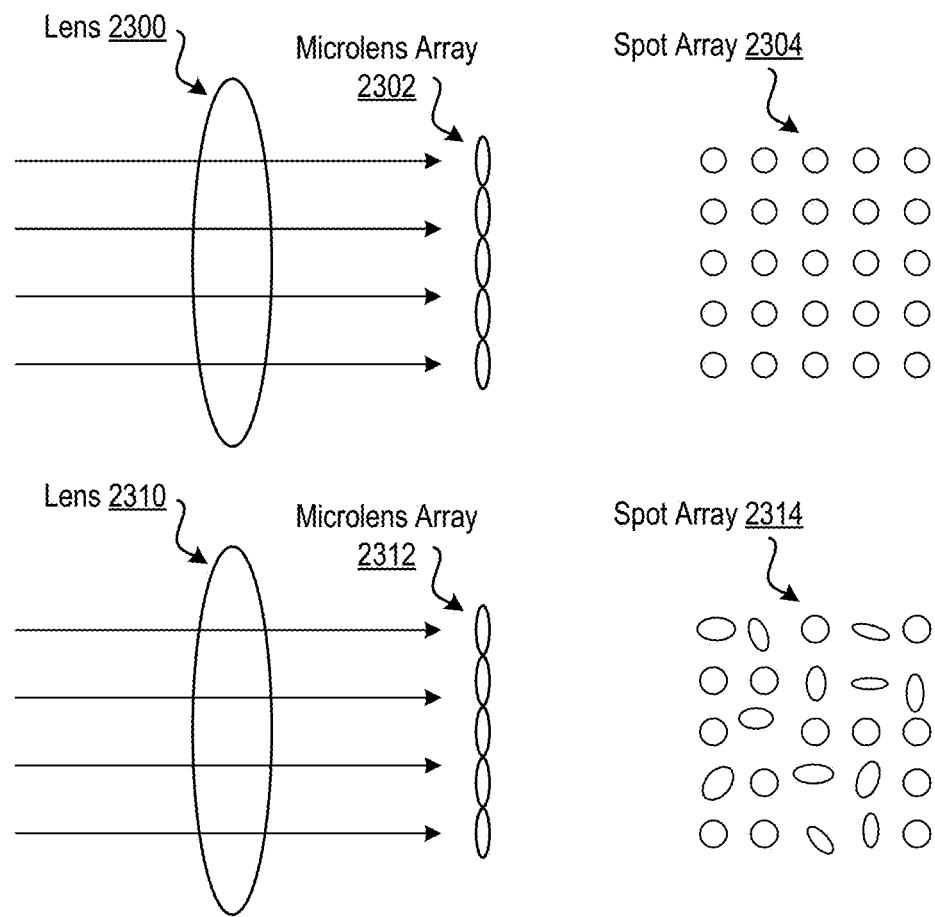
FIG. 23 illustrates example spot patterns acquired from lens measurements in accordance with an embodiment of the present disclosure.

FIG. 23 illustrates example spot patterns acquired from lens measurements in accordance with an embodiment of the present disclosure. Lens 2300 represents a non-prescription lens, or a lens having a known prescription. When light passes through the lens 2300 and a microlens array 2302, the resulting spot array 2304 captured by a light detector will include an array of evenly distributed spots. Lens 2310 represents a lens having an unknown prescription. When light passes through the lens 2310 and a microlens array 2312, the resulting spot array 2314 captured by the light detector will include an array of distorted spots. The spot array 2314 of the unknown prescription lens 2310 can be compared to the spot array 2304 of the non-prescription (or known prescription) lens 2300 using mathematical transformations known in the art by a processing device to determine the prescription of the lens 2310.

Figure 24:
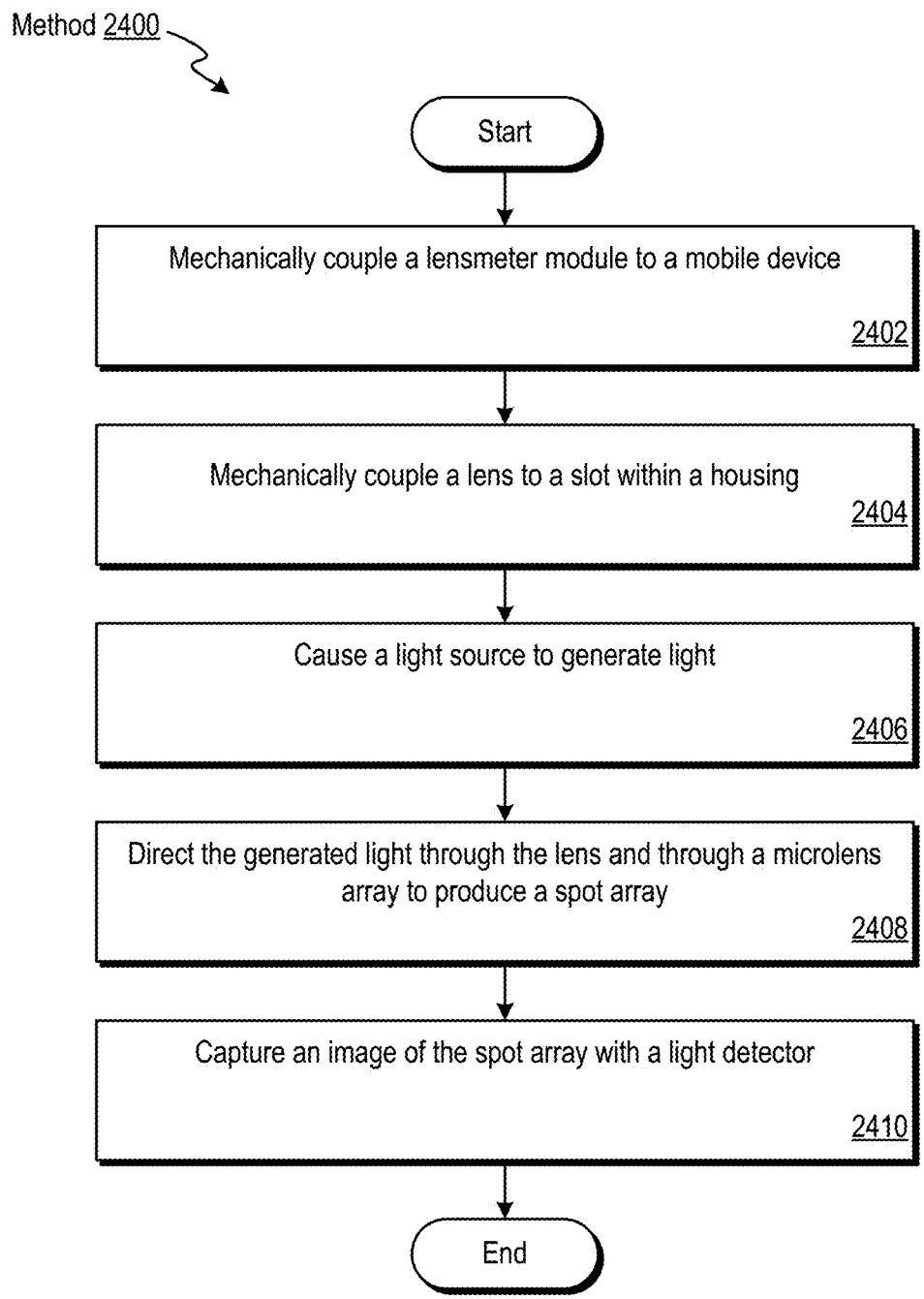
FIG. 24 is a block diagram illustrating a method for determining a prescription of a lens according to an embodiment of the present disclosure.

FIG. 24 is a block diagram illustrating a method 2400 for determining a prescription of a lens according to an embodiment of the present disclosure. For example, method 2400 and variants thereof may be performed using the portable lensmeters 1900, 2000, or 2100 described with respect to FIGS. 19-21.

At block 2402, a lensmeter module (e.g., illustrated as housing 2002) is mechanically coupled to a mobile device (e.g., mobile device 2010). In certain embodiments, a housing of the lensmeter module is in a form of an extended shaft (e.g., shaft 2252) having a proximal end and a distal end. The lensmeter module may include a connector (e.g., slot 2012, connector 2262, etc.) located at the distal end of the extended shaft, with the lensmeter module being mechanically coupled to the mobile device via the connector. In certain embodiments, the connector includes a plate (e.g., plate 2260) having a proximal surface and a distal surface, with the extended shaft (e.g., shaft 2252) being a contiguous extension that extends proximally from the proximal surface of the plate. The distal end of the extended shaft defines an opening through the plate, and the distal surface of the plate abuts at least a portion of a surface of the mobile device.

In certain embodiments, block 2402 may be omitted, for example, when the portable lensmeter is a self-contained lensmeter (e.g., portable lensmeter 1900).

At block 2404, a lens (e.g., lenses 1908 or 2264) is mechanically coupled to a slot (e.g., slots 1914 or 2254) within the housing of the lensmeter or lensmeter module. The lens may be a lens of a pair of glasses, and may have an unknown prescription. In certain embodiments, the lens may have a known prescription, and captured data for the lens may be used at a later time to determine a prescription of an unknown lens.

At block 2406, a light source generates light. In certain embodiments, the light source is contained within the housing (e.g., light sources 1954 or 2054). The internally-produced light may be generated in response to a processing device (e.g., processing devices 1950 or 2050) activating the light source or in response to manual activation of the light source by a patient, medical practitioner, or technician (e.g., by pressing a button or a switch). In certain embodiments, the light source is a light source of a mobile device (e.g., light source 2154).

At block 2408, the generated light is directed through the lens and through a microlens array (e.g., microlens array 1910) to produce a spot array.

At block 2410, an image of the spot array is captured by a light detector (e.g., light detectors 1912, 2008, or 2108). In certain embodiments, an image of the captured light is transmitted (e.g., via processing devices 1950 or 2050) to a remote device for storage, processing, or analysis. In certain embodiments, the captured light is processed by the processing device within the housing or by a processing device of the mobile device. In certain embodiments, the microlens array includes a total number of lenses ranging from 25 to 400. In certain embodiments, the processing device determines a prescription of the lens based on the captured image of the spot array, for example, by comparing the captured image to a spot array image representative of a lens having a known prescription.

General Computer System Embodiments

Figure 25:
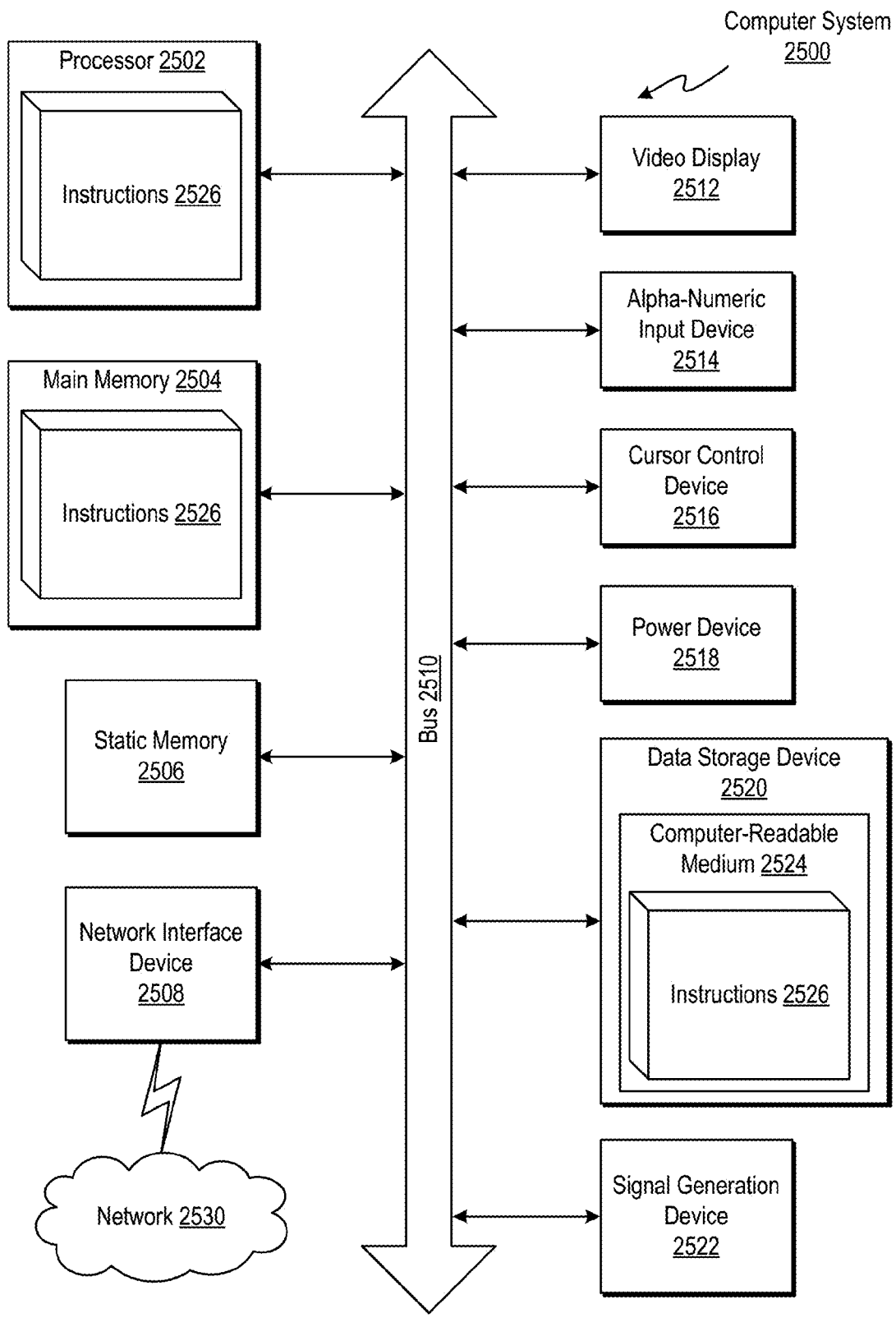
FIG. 25 is an illustrative computer system that certain embodiments of the disclosure may utilize.

FIG. 25 illustrates a diagrammatic representation of a machine in the exemplary form of a computer system 2500 within which a set of instructions (e.g., for causing the machine to perform or facilitate performance of any one or more of the methodologies discussed herein) may be executed. In alternative embodiments, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Some or all of the components of the computer system 2500 may be utilized by or illustrative of any of the processing devices described herein (e.g., processing device 350), the mobile devices (e.g., mobile device 410), or any other devices that may send/receive information to/from any of the devices described herein.

The exemplary computer system 2500 includes a processing device (processor) 2502, a main memory 2504 (e.g., read-only memory (ROM), flash memory, dynamic random access memory (DRAM) such as synchronous DRAM (SDRAM) or Rambus DRAM (RDRAM), etc.), a static memory 2506 (e.g., flash memory, static random access memory (SRAM), etc.), and a data storage device 2520, which communicate with each other via a bus 2510.

Processor 2502 represents one or more general-purpose processing devices such as a microprocessor, central processing unit, or the like. More particularly, the processor 2502 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 2502 may also be one or more special-purpose processing devices such as an application specific integrated circuit (ASIC), a field programmable gate array (FPGA), a digital signal processor (DSP), network processor, or the like. The processor 2502 is configured to execute instructions 2526 for performing the operations and steps discussed herein.

The computer system 2500 may further include a network interface device 2508. The computer system 2500 also may include a video display unit 2512 (e.g., a liquid crystal display (LCD), a cathode ray tube (CRT), or a touch screen), an alphanumeric input device 2514 (e.g., a keyboard), a cursor control device 2516 (e.g., a mouse), and a signal generation device 2522 (e.g., a speaker).

Power device 2518 may monitor a power level of a battery (e.g., battery 352) used to power the computer system 2500 or one or more of its components. The power device 2518 may provide one or more interfaces to provide an indication of a power level, a time window remaining prior to shutdown of computer system 2500 or one or more of its components, a power consumption rate, an indicator of whether computer system is utilizing an external power source or battery power, and other power related information. In certain embodiments, indications related to the power device 2518 may be accessible remotely (e.g., accessible to a remote back-up management module via a network connection). In certain embodiments, a battery utilized by the power device 2518 may be an uninterruptible power supply (UPS) local to or remote from computer system 2500. In such embodiments, the power device 2518 may provide information about a power level of the UPS.

The data storage device 2520 may include a computer-readable storage medium 2524 on which is stored one or more sets of instructions 2526 (e.g., software) embodying any one or more of the methodologies or functions described herein. The instructions 2526 may also reside, completely or at least partially, within the main memory 2504 and/or within the processor 2502 during execution thereof by the computer system 2500, the main memory 2504 and the processor 2502 also constituting computer-readable storage media. The instructions 2526 may further be transmitted or received over a network 2530 via the network interface device 2508.

In one embodiment, the instructions 2526 include instructions for performing various electronic operations, such as processing image data and/or controlling the operation of components within an optical device. While the computer-readable storage medium 2524 is shown in an exemplary embodiment to be a single medium, the terms "computer-readable storage medium" or "machine-readable storage medium" should be taken to include a single medium or multiple media (e.g., a centralized or distributed database, and/or associated caches and servers) that store the one or more sets of instructions. The terms "computer-readable storage medium" or "machine-readable storage medium" shall also be taken to include any transitory or non-transitory medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description may have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is herein, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities.

Unless specifically stated otherwise as apparent from the preceding discussion, it is appreciated that throughout the description, discussions utilizing terms such as "receiving," "storing," "transmitting," "computing," "processing," "analyzing," "generating," "displaying," "rendering for display," "activating," "deactivating," "controlling," or the like, refer to the actions and processes of a computer system, or similar electronic computing device. The actions may be used by the computer system, or similar electronic computing device, to manipulate and transform data represented as physical (e.g., electronic) quantities within the computer system's registers and memories into other data similarly represented as physical quantities within the computer system memories or registers or other such information storage, transmission, or display devices. The actions may also be used by the computer system, or similar electronic computing device, to control the operation of other electronic devices.

Certain embodiments of the disclosure relate to an apparatus, device, or system for performing the operations herein. This apparatus, device, or system may be specially constructed for the required purposes, or it may include a general purpose computer selectively activated or reconfigured by a computer program stored in the computer. Such a computer program may be stored in a computer- or machine-readable storage medium, such as, but not limited to, any type of disk including floppy disks, optical disks, compact disk read-only memories (CD-ROMs), and magnetic-optical disks, read-only memories (ROMs), random access memories (RAMs), erasable programmable read-only memories (EPROMs), electrically erasable programmable read-only memories (EEPROMs), magnetic or optical cards, or any type of media suitable for storing electronic instructions.

For simplicity of explanation, the methods of the present disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. Additionally, it should be appreciated that algorithms disclosed in this specification are capable of being stored on an article of manufacture to facilitate transporting and transferring such algorithms to computing devices for execution. The term "article of manufacture", as used herein, is intended to encompass a computer program accessible from any computer-readable device or storage media.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment" or "one embodiment" means that a particular feature, structure, or characteristic described in connection with the embodiment is included in at least one embodiment. Thus, the appearances of the phrase "an embodiment" or "one embodiment" in various places throughout this specification are not necessarily all referring to the same embodiment.

It is to be understood that the above description is intended to be illustrative, and is not intended to be limited by the specific embodiments described herein or by way of illustration in the accompanying drawings. Indeed, other various embodiments of and modifications to the present disclosure, in addition to those described herein, will be apparent to those of ordinary skill in the art from the preceding description and accompanying drawings. Thus, such other embodiments and modifications pertaining to optical analysis of a patient's eye are intended to fall within the scope of the present disclosure. Further, although the present disclosure has been described herein in the context of particular embodiments in particular environments for particular purposes, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein, along with the full scope of equivalents to which such claims are entitled.

What is claimed is:

1. A corneal topographer module for analyzing a cornea of a patient's eye, the corneal topographer module being adapted to mechanically couple to a mobile device comprising a light detector, the corneal topographer module comprising:
    a housing having a first aperture and a second aperture formed therethrough; and
    a plurality of optical components disposed within the housing, the plurality of optical components being arranged to:
        form a light beam having a diameter of at least 9 millimeters from light generated by a light source;
        direct the light beam through the first aperture to the cornea via a first optical channel when the cornea is located adjacent to the first aperture; and
        direct reflected light from the cornea into the housing through the first aperture and to the light detector via a second optical channel when the corneal topographer module is mechanically coupled to the mobile device.

2. The corneal topographer module of claim 1, wherein the housing is in a form of an extended shaft having a proximal end and a distal end, wherein the first aperture is located at the proximal end and the second aperture is located at the distal end, and wherein the corneal topographer module comprises a connector located at the distal end of the extended shaft.

3. The corneal topographer module of claim 2, wherein the connector comprises a plate having a proximal surface and a distal surface, wherein the extended shaft is a contiguous extension that extends proximally from the proximal surface of the plate, wherein the distal end of the extended shaft defines an opening through the plate, and wherein the distal surface of the plate abuts at least a portion of a surface of the mobile device when the second aperture is positioned adjacent to the light detector of the mobile device.

4. The corneal topographer module of claim 2, wherein the connector comprises a slot for receiving and mechanically coupling to the mobile device.

5. The corneal topographer module of claim 1, wherein the plurality of optical components comprise a microlens array arranged to define a portion of the second optical channel.

6. The corneal topographer module of claim 1, wherein the housing has a third aperture formed therethrough, and wherein the plurality of optical components are further arranged to direct light received into the housing through the third aperture to the first aperture via a third optical channel.

7. The corneal topographer module of claim 6, wherein the plurality of optical components comprises an alignment target located at a focal point of the third optical channel.

8. The corneal topographer module of claim 7, wherein the alignment target comprises a transparent disc having a non-transparent mark formed thereon, wherein the alignment target is arranged such that the non-transparent mark is centered on an optical axis defined by the third optical channel.

9. The corneal topographer module of claim 1, further comprising the light source, wherein the light source comprises a laser disposed within the housing.

10. A corneal topographer for analyzing a cornea of a patient's eye, the corneal topographer comprising:
    a housing having a first aperture and a second aperture formed therethrough; and a plurality of optical components disposed within the housing, the plurality of optical components being arranged to:
- form a light beam having a diameter of at least 9 millimeters from light generated by a light source;
- direct the light beam through the first aperture to the cornea via a first optical channel when the cornea is located adjacent to the first aperture;
- direct light received into the housing through the second aperture to the first aperture via a second optical channel; and
- direct reflected light from the cornea into the housing through the first aperture and to a light detector via a third optical channel, wherein the third optical channel is adapted to project the reflected light onto the light detector to capture an image of the reflected light.

11. A method comprising:
mechanically coupling a corneal topographer module to a mobile device;
causing a light source housed within a housing of the corneal topographer module to produce internally-produced light;
forming a light beam having a diameter of at least 9 millimeters from the internally-produced light;
directing the light beam through the housing and to a cornea of a patient; and
capturing, with a light detector of the mobile device, reflected light from the cornea of the patient.

12. The method of claim 11, further comprising:
directing the reflected light through a microlens array prior to capturing the reflected light with the light detector; and
transforming, by a processing device, the captured reflected light into a topographical image of the cornea.

13. The method of claim 11, further comprising:
receiving externally-produced light into the housing via an aperture of the housing; and
simultaneously directing the light beam and the externally-produced light through the housing and to the cornea of the patient.

14. The method of claim 13, wherein the externally-produced light comprises light reflected off of an object located at least 4 meters from the aperture of the housing.

15. The method of claim 14, further comprising:
directing the externally-produced light through an alignment target disposed within the housing prior to the externally-produced light reaching the cornea of the patient, wherein the reflected light corresponds to light reflected off of the cornea of the patient as the patient is focusing on the object using the alignment target.

16. The method of claim 15, wherein the alignment target comprises a transparent disc having a non-transparent mark formed thereon.

17. The method of claim 11, wherein the housing is in a form of an extended shaft having a proximal end and a distal end, wherein the corneal topographer module comprises a connector located at the distal end of the extended shaft, and the corneal topographer module is mechanically coupled to the mobile device via the connector.

18. The method of claim 17, wherein the connector comprises a plate having a proximal surface and a distal surface, wherein the extended shaft is a contiguous extension that extends proximally from the proximal surface of the plate, wherein the distal end of the extended shaft defines an opening through the plate, and wherein the distal surface of the plate abuts at least a portion of a surface of the mobile device.

19. The method of claim 17, wherein the connector comprises a slot for receiving and mechanically coupling the corneal topographer module to the mobile device.

* * * * *